United States Patent
Sakaki et al.

[11] Patent Number: 6,022,893
[45] Date of Patent: Feb. 8, 2000

[54] HYDROXAMIC ACID DERIVATIVES

[75] Inventors: Katsuhito Sakaki; Hidekazu Kanazawa; Tsuneyuki Sugiura; Tohru Miyazaki; Hiroyukii Ohno, all of Osaka, Japan

[73] Assignee: ONO Pharmaceutical Co., Ltd., Osaka, Japan

[21] Appl. No.: 08/694,473

[22] Filed: Aug. 7, 1996

[30] Foreign Application Priority Data

Aug. 8, 1995 [JP] Japan .................................. 7-222673

[51] Int. Cl.$^7$ ...................... C07C 311/41; A61K 31/215
[52] U.S. Cl. ........................ 514/507; 514/575; 548/495; 549/72; 560/312; 562/623
[58] Field of Search ........................... 560/312; 562/623; 514/507, 575; 548/495; 549/72

[56] References Cited

U.S. PATENT DOCUMENTS

| | | |
|---|---|---|
| 2,868,691 | 1/1959 | Porush et al. |
| 3,095,355 | 6/1963 | Aramson et al. |
| 3,316,257 | 4/1967 | Ohnacker . |
| 4,146,716 | 3/1979 | Cox et al. |
| 4,196,207 | 4/1980 | Webber . |
| 4,435,566 | 3/1984 | Ohno et al. |
| 5,017,610 | 5/1991 | Imaki et al. |
| 5,455,258 | 10/1995 | MacPherson et al. ................ 514/357 |

FOREIGN PATENT DOCUMENTS

| | | |
|---|---|---|
| 0082023 | 6/1983 | European Pat. Off. |
| 0248413 | 12/1987 | European Pat. Off. |
| 0347146 | 12/1989 | European Pat. Off. |
| 347168A1 | 12/1989 | European Pat. Off. |
| 0441339 | 8/1991 | European Pat. Off. |
| 0447891 | 9/1991 | European Pat. Off. |
| 0452002 | 10/1991 | European Pat. Off. |
| 0579496 | 1/1994 | European Pat. Off. |
| 0607439 | 7/1994 | European Pat. Off. |
| 606046A1 | 7/1994 | European Pat. Off. |
| 1065317 | 4/1967 | United Kingdom . |
| 2157684 | 10/1985 | United Kingdom . |
| 9422855 | 10/1994 | WIPO . |
| 9535275 | 12/1995 | WIPO . |
| 9535276 | 12/1995 | WIPO . |
| 9600214 | 1/1996 | WIPO . |

OTHER PUBLICATIONS

Inhibitors of matrix metalloproteinases (MMP's), Beeley et al, Curr. Opin. Ther. Patents (1994) 4(1):7–16, Current Drugs Ltd. ISSN 0962–2594.

*Primary Examiner*—Robert Gerstl
*Attorney, Agent, or Firm*—Stevens, Davis, Miller & Mosher, L.L.P.

[57] ABSTRACT

The present invention relates to:

(i) hydroxamic acid derivative of the formula (I):

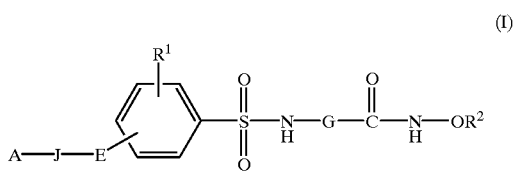

wherein $R^1$ is hydrogen, or C1–4 alkyl; $R^2$ is hydrogen, C1–8 alkyl, phenyl, C1–4 alkyl substituted by phenyl; E is —CONR$^3$—, in which $R^3$ is hydrogen, C1–4 alkyl, etc., —NR$^3$CO—, —CO—O—, —O—CO—etc.; A is hydrogen, C1–8 alkyl, C3–7 cycloalkyl, or Ar; J is bond, C2–4 alkylene etc.; G is —(CH$_2$)$_m$—, in which m is 2, 3 or 4, or

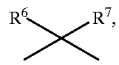

in which $R^6$ and $R^7$ is hydrogen, C1–8 alkyl etc.; and non-toxic salts thereof, ii) processes for the preparation thereof, and iii) pharmaceutical agents containing them.

The compounds of formula (I) are useful for prevention and/or treatment of diseases induced by overexpression or excess activity of gelatinases, for example, rheumatoid diseases, arthrosteitis, unusual bone resorption, osteoporosis, periodontitis, interstitial nephritis, arteriosclerosis, pulmonary emphysema, cirrhosis, cornea injury, metastasis of, invasion of or growth of tumor cells, autoimmune disease (Crohn's disease, Sjogren's syndrome), disease caused by vascular emigration or infiltration of leukocytes or arterialization in animals including human beings, especially human beings.

6 Claims, No Drawings

HYDROXAMIC ACID DERIVATIVES

SUMMARY

This invention relates to hydroxamic acid derivatives. More particularly, this invention relates to:

(i) hydroxamic acid derivatives of the formula (I):

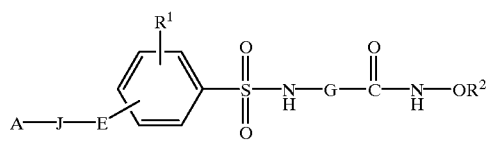

(I)

wherein all the symbols are the same meaning as hereinafter defined, and non-toxic salts thereof, (ii) processes for the preparation thereof, and (iii) pharmaceutical agent containing them.

BACKGROUND

The matrix metalloproteinases (MMPs) are neutral metalloproteinases and zinc ($Zn^{2+}$) is essential in the active site for their activation. They degrade collagen, laminin, proteoglycans, fibronectin, elastin, gelatin etc. under physiological conditions and therefore, are effective on growth and tissue remodeling of articulation tissue, bone tissue and connective tissue. At least 10 classes of MMPs which differ in primary structure are identified. As common characteristics of these enzymes, MMPs (1) have $Zn^{2+}$ in the active site and the activity depends on calcium ($Ca^{2+}$), (2) are secreted as an inactive proenzyme and activated outside of cells, (3) have high homology on amino acid sequence, (4) have an ability to degrade various extracellular matrix components in vivo, (5) are regulated by tissue inhibitors of metalloproteinases (TIMP) which are specific to MMPs.

Recently, it is reported that gelatinases, neutral metalloproteinases classified in MMPs which degrade various extracellular matrix represented by gelatin are related to various diseases.

Gelatinase inhibitors are useful for prevention and/or treatment of various diseases induced by overexpression or excess activation of gelatinases. Such diseases are, for example, rheumatoid diseases, arthrosteitis, unusual bone resorption, osteoporosis, periodontitis, interstitial nephritis, arteriosclerosis, pulmonary emphysema, cirrhosis, cornea injury, metastasis of, invasion of or growth of tumor cells, autoimmune diseases (e.g. Crohn's disease, Sjogren's syndrome), diseases caused by vascular emigration or infiltration of leukocytes, arterialization.

RELATED ARTS

Some compounds possessing inhibitory activity against gelatinases are known. Much research and development on substrate analogous MMP inhibitors has energetically been carried out [Inhibitors of matrix metalloproteinases (MMP's), Nigel R A Beeley, Phillip R J Ansell, Andrew J P Docherty et. al., Curr. Opin. Ther. Patents., 4, 7–16 (1994), Current Drugs Ltd ISSN 0962-2594].

For example, in the specification of EP 606046, arylsulfonamide derivatives of the formula (X):

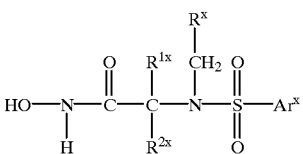

(X)

wherein (a) $Ar^x$ is carbocyclic or heterocyclic aryl; $R^x$ is hydrogen, lower alkyl, carbocyclic aryl-lower alkyl etc.; $R^{1x}$ is hydrogen, lower alkyl, carbocyclic aryl-lower alkyl etc.; $R^{2x}$ is hydrogen, lower alkyl; or (b) $R^x$ and $R^{1x}$ together with the chain to which they are attached form 1, 2, 3, 4-tetrahydro-isoquinoline, piperidine etc.; $Ar^x$ and $R^{2x}$ are as defined in (a); or (c) $R^{1x}$ and $R^{2x}$ together with the carbon to which they are attached form C3–7 cycloalkane, oxa-cyclohexane, thia-cyclohexane etc. which is unsubstituted or substituted by lower alkyl;

and $Ar^x$ and $R^{2x}$ are as defined in (a);

are disclosed to have inhibitory activity against matrix metalloproteinase.

PURPOSE OF INVENTION

Energetic investigations have been carried out in order to make a gelatinase inhibitor. The present inventors have found that a series of hydroxainic acid derivatives of the formula (I) have inhibitory activity against gelatinases and have accomplished the present invention.

Hydroxamic acid derivatives of the formula (I) of the present invention are novel compounds that are not known at all.

DISCLOSURE OF THE INVENTION

The present invention relates to:

(i) hydroxamic acid derivative of formula (I):

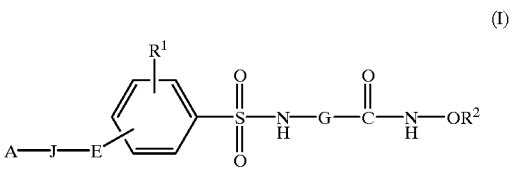

(I)

wherein $R^1$ is hydrogen, or C1–4 alkyl;

$R^2$ is (1) hydrogen, (2) C1–8 alkyl, (3) phenyl, or (4) C1–4 alkyl substituted by phenyl;

E is (1) —$CONR^3$—, in which $R^3$ is as hydrogen, C1–4 alkyl, phenyl, or C1–4 alkyl substituted by phenyl;

(2) —$NR^3CO$—, in which $R^3$ is as hereinbefore defined;

(3) —CO—O—, (4) —O—CO—, (5) —$NR^3$—CO—$NR^3$—, in which $R^3$ is as hereinbefore defined;

(6) —CO—$CH_2$—, (7) —CO—, (8) —O—CO—$NR^3$—, in which $R^3$ is as hereinbefore defined;

(9) —$NR^3$—CO—O—, in which $R^3$ is as hereinbefore defined;

(10) —O—CO—O—,

(11) —CS—$NR^3$—, in which $R^3$ is as hereinbefore defined;

(12) —NR³—CS—, in which R³ is as hereinbefore defined;
(13) —NR³—CS—NR³—, in which R³ is as hereinbefore defined;
(14) —O—CS—NR³—, in which R³ is as hereinbefore defined;
(15) —NR³—CS—O—, in which R³ is as hereinbefore defined;
(16) —CS—O,
(17) —O—CS—, or,
(18) —O—CS—O—, A is (1) hydrogen, (2) C1–8 alkyl, (3) C3–7 cycloalkyl, or (4) Ar, in which Ar is carbocyclic aryl or heterocyclic aryl, and is unsubstituted or substituted by 1–3 of C1–15 alkyl, C1–15 alkoxy, halogen, nitro, cyano, guanidino, amidino, hydroxy, benzyloxy, —NR⁹R¹⁰, in which R⁹ and R¹⁰ each, independently, is hydrogen or C1–4 alkyl; —COOR¹¹, in which R¹¹ is hydrogen or C1–4 alkyl; trifluoromethyl, phenyl or heterocyclic ring;

J is (1) a bond, (2) C2–4 alkylene, (3) C2–4 alkenylene, or (4)

in which R⁴ and R⁵ each, independently, is (i) hydrogen, (ii) C1–4 alkyl, or (iii) C1–4 alkoxy, or R⁴ and R⁵, taken together with the carbon to which they are attached, form a C3–7 cycloalkyl group, G is (1) —(CH₂)$_m$—, in which m is 2, 3 or 4, or (2)

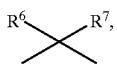

in which R⁶ and R⁷ each, independently, is (i) hydrogen, (ii) C1–8 alkyl, (iii) —COOR⁸, in which R⁸ is hydrogen, C1–8 alkyl, phenyl, or C1–4 alkyl substituted by phenyl; (iv) Ar, in which Ar is as hereinbefore defined; (v) heterocyclic ring, (vi) C1–8 alkyl substituted by: —COOR⁸, in which R⁸ is as hereinbefore defined; C1–4 alkoxy; hydroxy; benzyloxy; —NR¹²R¹³, in which R¹² and R¹³ each, independently, is hydrogen or C1–4 alkyl; —NR¹⁴COOR¹⁵, in which R¹⁴ is hydrogen or C1–4 alkyl, and R¹⁵ is hydrogen, C1–8 alkyl, phenyl, or C1–4 alkyl substituted by phenyl; Ar; or heterocyclic ring; with the proviso that one of the carbon atoms in C1–8 alkyl may be replaced by a sulfur atom; or R⁶ and R⁷, taken together with the carbon to which they are attached, form a C3–7 cycloalkyl group; with the proviso that, the compounds in which E is —O—CO—NR³—, —O—CO—O—, —O—CS—NR³— or —O—CS—O—, J is a bond and A is hydrogen are excluded; and non-toxic salts thereof, ii) a processes for the preparation of a compound of formula (I) or non-toxic salt thereof, and iii) a pharmaceutical agents containing a compound of formula (I) or non-toxic salt thereof.

Unless otherwise specified, all isomers are included in the present invention. For example, alkyl, alkoxy and alkylene include straight and branched isomers. Isomers resulting from the presence of asymmetric carbon(s) e.g. branched alkyl, alkoxy and alkylene are also included within the present invention.

In the formula (I), C1–4 alkyl represented by R¹, R³, R⁴, R⁵, R⁹, R¹⁰, R¹¹, R¹², R¹³ or R¹⁴ means methyl, ethyl, propyl, butyl and isomeric groups thereof.

In the formula (I), C1–8 alkyl represented by R², R⁶, R⁷, R⁸, R¹⁵ or A means methyl, ethyl, propyl, butyl, pentyl, hexyl, heptyl, octyl and isomeric groups thereof.

In the formula (I), C1–4 alkyl substituted by phenyl represented by R², R³, R⁸ or R¹⁵ means methyl, ethyl, propyl, butyl and isomeric groups thereof substituted by 1 of phenyl.

In the formula (I), C1–4 alkoxy represented by R⁴, R⁵, R⁶ or R⁷ means methoxy, ethoxy, propoxy, butoxy and isomeric groups thereof.

In the formula (I), C1–15 alkyl as a substituent of Ar means methyl, ethyl, propyl, butyl, pentyl, hexyl, heptyl, octyl, nonyl, decyl, undecyl, dodecyl, tridecyl, tetradecyl, pentadecyl and isomeric groups thereof.

In the formula (I), C1–15 alkoxy as a substituent of Ar means methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy and isomeric groups thereof.

In the formula (I), halogen as a substituent of Ar is fluorine, chlorine, bromine or iodine.

In the formula (I), C2–4 alkylene represented by J means ethylene, trimethylene, tetramethylene and isomeric groups thereof.

In the formula (I), C2–4 alkenylene represented by J means vinylene, propenylene, butenylene, butadienylene and isomeric groups thereof.

In the formula (I), C3–7 cycloalkyl represented by R⁴ and R⁵, taken together with carbon to which they are attached, or by R⁶ and R⁷, taken together with carbon to which they are attached or by A means cyclopropyl, cyclobutyl, cyclopentyl, cyclohexyl and cycloheptyl.

In the formula (I), carbocyclic aryl represented by A, or by Ar in R⁶ and R⁷ preferably means C5–10 carbocyclic aryl, for example, benzene, pentalene, indene, naphthalene, azulene.

In the formula (I), heterocyclic aryl represented by A, or by in R⁶ and R⁷ preferably means C5–15 membered mono- or bi-heterocyclic aryl containing 1–2 of nitrogen and/or 1 of oxygen and/or 1 of sulfur, for example, a radical derived from pyrrole, imidazole, pyrazole, pyridine, pyrazine, pyrimidine, pyridazine, azepine, diazepine, furan, pyran, oxepin, oxazepine, thiophene, thiain (thiopyran), thiepin, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole or benzoimidazole.

In the formula (I), heterocyclic ring represented by R6 or R⁷, or present as a substituent of Ar, preferably means C5–15 membered mono- or bi-heterocyclic ring containing 1–2 of nitrogen and/or 1 of oxygen and/or 1 of sulfur. The heterocyclic ring includes partially or fully saturated analogues of the above C5–15 membered mono- or bi-heterocyclic aryl containing 1–2 of nitrogen and/or 1 of oxygen and/or 1 of sulfur, for example, a radical derived from pyrroline, pyrrolidine, imidazoline, imidazolidine, pyrazoline, pyrazolidine, piperidine, piperazine, tetrahydropyrimidine, tetrahydropyridazine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, morpholine, thiomorpholine, indoline, isoindoline, dihydrobenzofuran, perhydrobenzofuran, dihydroisobenzofuran, perhydrobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole or perhydrobenzimidazole.

In the present specification, including the claims, it is to be understood that the group E, as written, bonds to benzene ring at the right side and to J at the left side. For example, when E is written as —CO—NR$^3$—, the group A—J—E— bonded to the benzene ring is A—J—CO—NR$^3$—.

Salts

Non-toxic salts of the present invention include all pharmaceutically acceptable salts, for example, general salts, acid addition salts, hydrate salts.

The compounds of the formula (I) of the present invention may be converted into the corresponding salts. Water-soluble salts are preferred.

Suitable salts, for example, include:

salts of alkali metals (e.g. sodium, potassium), salts of alkaline earth metals (e.g. calcium, magnesium), ammonium salts, salts of pharmaceutically acceptable organic amines (e.g. tetramethylammonium, triethylamine, methylamine, dimethylamine, cyclopentylamine, benzylamine, phenethylamine, piperidine, monoethanolamine, diethanolamine, tris (hydroxymethyl)amine, lysine, arginine, N-methyl-D-glucamine).

The compounds of the formula (I) may be converted into the corresponding acid addition salts. Water-soluble salts are preferred. Suitable salts, for example, include:

salts of inorganic acids e.g. hydrochloride, hydrobromide, hydroiodide, sulfate, phosphate, nitrate; salts of organic acids e.g. acetate, trifluoroacetate, lactate, tartarate, oxalate, fumarate, maleate, citrate, benzoate, methanesulphonate, ethanesulphonate, benzenesulphonate, toluenesulphonate, isethionate, glucuronate, gluconate.

The compounds of the formula (I) and salts thereof may be converted into the corresponding hydrates by conventional means.

In the compound of the present invention of the formula (I), hydroxamic acid derivatives of the following formulae, and non-toxic salts thereof are preferred:

the formula I(1):

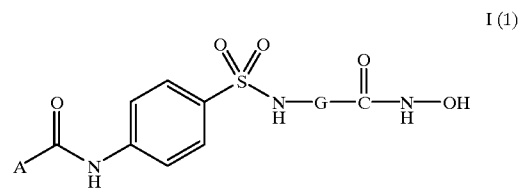

I(1)

wherein A and G are as hereinbefore defined, the formula I(2):

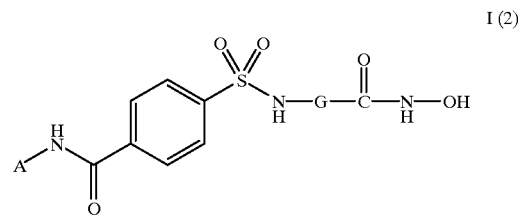

I(2)

wherein A and G are as hereinbefore defined, the formula I(3):

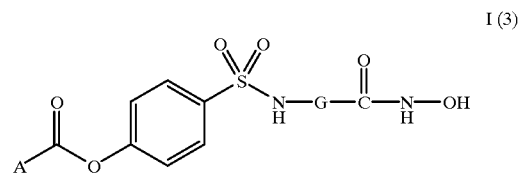

I(3)

wherein A and G are as hereinbefore defined, the formula I(4):

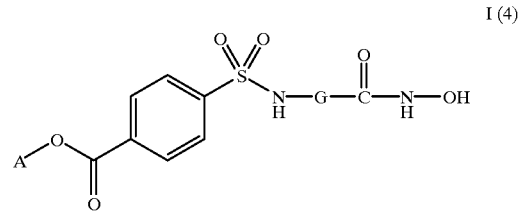

I(4)

wherein A and G are as hereinbefore defined, the formula I(5):

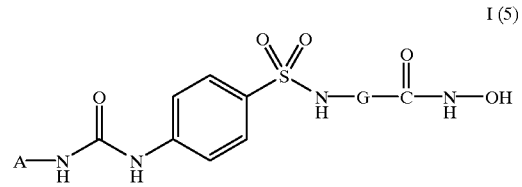

I(5)

wherein A and G are as hereinbefore defined, the formula I(6):

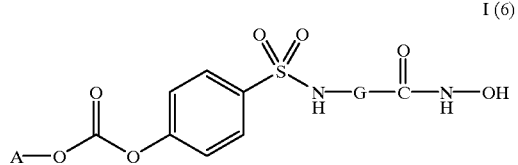

wherein A and G are as hereinbefore defined,
the formula I(7):

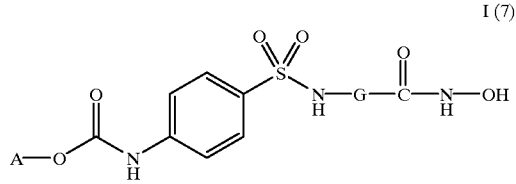

wherein A and G are as hereinbefore defined,
the formula I(8):

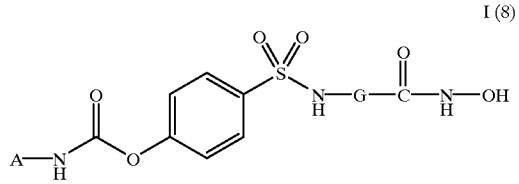

wherein A and G are as hereinbefore defined,
the formula I(9):

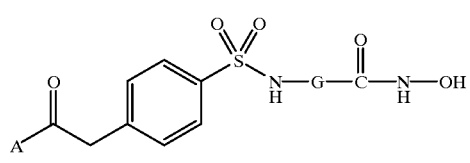

wherein A and G are as hereinbefore defined,
the formula I(10):

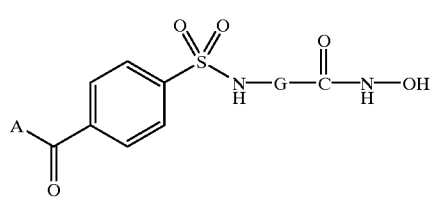

wherein A and G are as hereinbefore defined, the formula I(11):

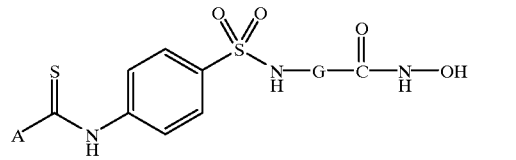

wherein A and G are as hereinbefore defined,
the formula I(12):
wherein A and G are as hereinbefore defined,
the formula I(13):

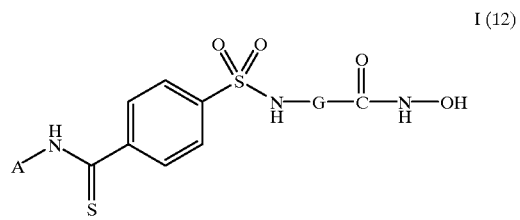

wherein A and G are as hereinbefore defined,
the formula I(14):0

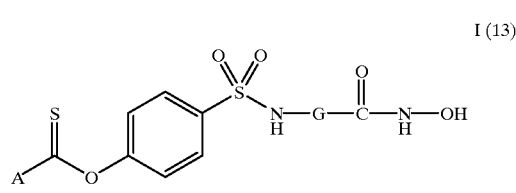

wherein A and G are as hereinbefore defined,
the formula I(15):

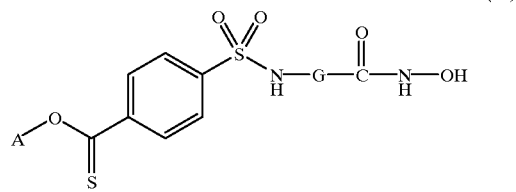

wherein A and G are as hereinbefore defined,
the formula I(15):

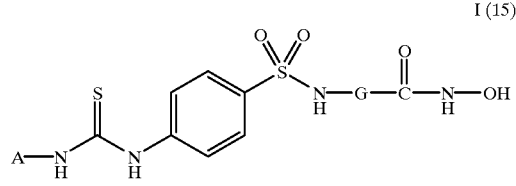

wherein A and G are as hereinbefore defined, the formula I(16):

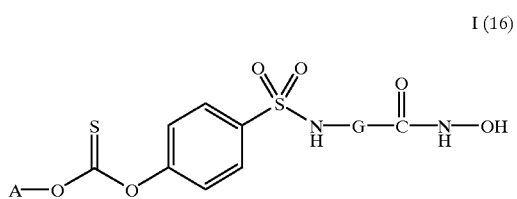

wherein A and G are as hereinbefore defined,
the formula I(17):

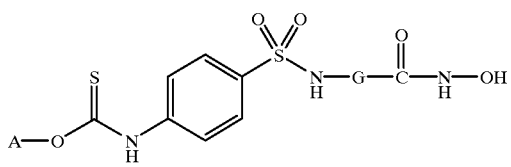

wherein A and G are as hereinbefore defined, the formula I(18):

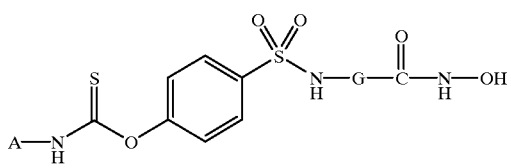

wherein A and G are as hereinbefore defined,
the formula I(19):

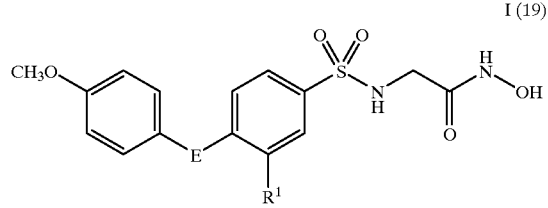

wherein $R^1$ and E are as hereinbefore defined,
the formula I(20):

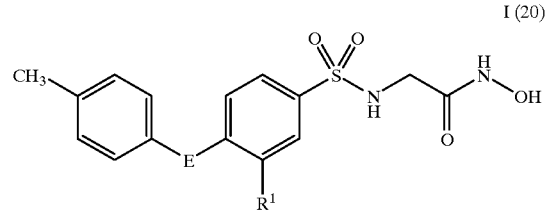

wherein $R^1$ and E are as hereinbefore defined, the formula I(21):

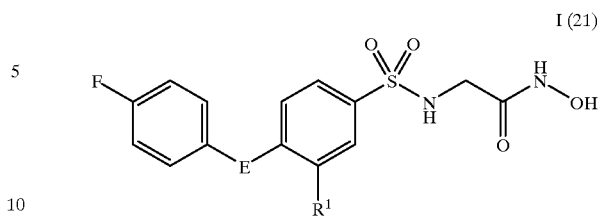

wherein $R^1$ and E are as hereinbefore defined, the formula I(22):

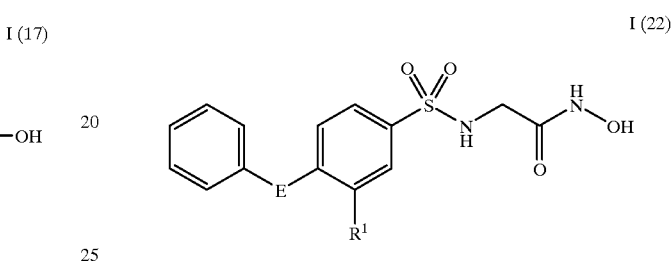

wherein A and G are as hereinbefore defined,
the formula I(23):

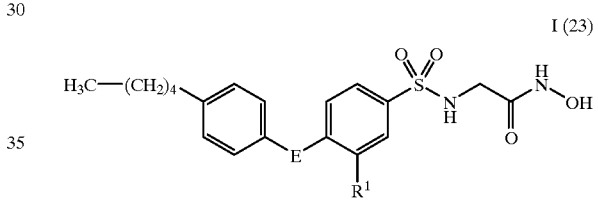

wherein $R^1$ and E are as hereinbefore defined.

The preferred specific compounds of the formula (I) are the compounds in Tables 1–23, the compounds described in the Examples and non-toxic salts thereof.

TABLE 1

(IA)

| No. | A | G |
|-----|---|---|
| 1 | phenyl | isopropyl-CH(CH₃) (branched) |
| 2 | phenyl | branched alkyl |

TABLE 1-continued (IA)

[Structure: A-C(=O)-NH-C6H4-S(=O)2-NH-G-C(=O)-NH-OH]

| No. | A | G |
|---|---|---|
| 3 | phenyl | -CH2-CH(CH3)-CH3 (isobutyl via CH2Ph) — benzyl-isobutyl (PhCH2CH(iPr)) |
| 4 | 4-methylphenyl | -CH(CH3)-CH(CH3)2 |
| 5 | 4-methylphenyl | -CH2-CH(CH3)-CH2-CH(CH3)2 |
| 6 | 4-methylphenyl | -CH2-C6H5 isobutyl-phenyl |
| 7 | 4-methylphenyl | 3-(1H-indolyl)methyl-isobutyl |
| 8 | 4-(n-pentyl)phenyl (H3C—(CH2)4—) | benzyl-isobutyl |
| 9 | pyridin-3-yl | -CH(CH3)-CH(CH3)2 |
| 10 | pyridin-3-yl | -CH2-CH(CH3)-CH2-CH(CH3)2 |
| 11 | pyridin-3-yl | benzyl-isobutyl |

TABLE 2

(IB)

[Structure: A-NH-C(=O)-C6H4-S(=O)2-NH-G-C(=O)-NH-OH]

| No. | A | G |
|---|---|---|
| 1 | phenyl | -CH(CH3)-CH(CH3)2 |
| 2 | phenyl | -CH2-CH(CH3)-CH2-CH(CH3)2 |
| 3 | phenyl | benzyl-isobutyl |
| 4 | 4-methylphenyl | -CH(CH3)-CH(CH3)2 |

TABLE 2-continued
(IB)
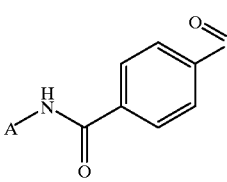
| No. | A | G |
|---|---|---|
| 5 | 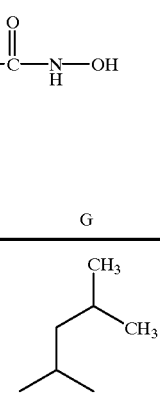 | 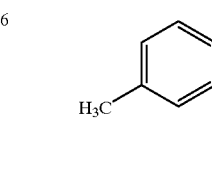 |
| 6 | 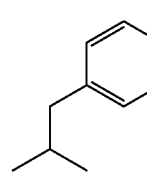 | 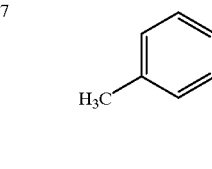 |
| 7 | 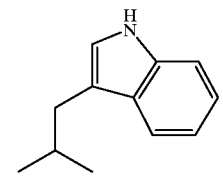 | 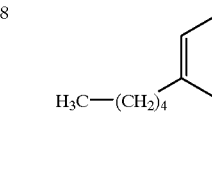 |
| 8 | 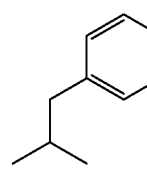 | 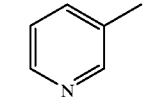 |
| 9 | 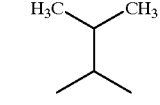 | 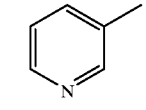 |
| 10 | 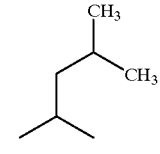 | 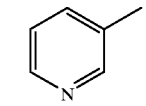 |
| 11 | 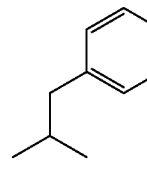 | 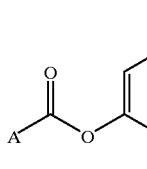 |
TABLE 3
(IC)
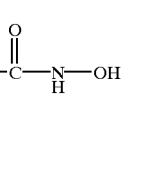
| No. | A | G |
|---|---|---|
| 1 | 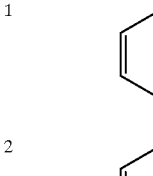 | 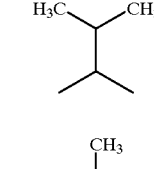 |
| 2 | 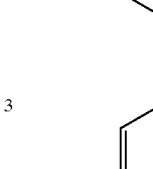 | 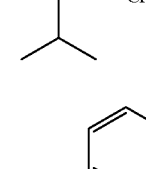 |
| 3 | 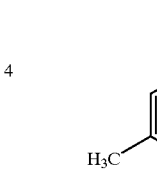 | 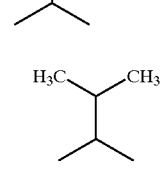 |
| 4 | 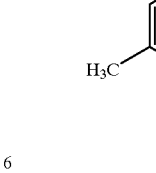 | 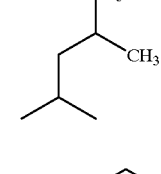 |
| 5 | 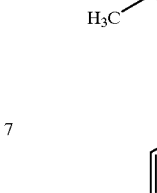 | 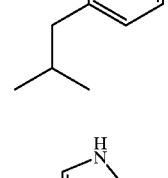 |
| 6 | 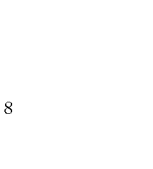 | 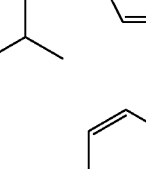 |
| 7 |  |  |
| 8 |  |  |

TABLE 3-continued (IC)

| No. | A | G |
|---|---|---|
| 9 | 3-pyridyl | isopropyl-CH(CH₃)- (H₃C-CH(CH₃)-CH(CH₃)-) |
| 10 | 3-pyridyl | -CH(CH₃)CH₂CH(CH₃)₂ |
| 11 | 3-pyridyl | -CH₂CH(CH₃)₂ attached to phenyl (benzyl-isobutyl) |

TABLE 4

(ID)

| No. | A | G |
|---|---|---|
| 1 | phenyl | H₃C-CH(CH₃)-CH(CH₃)- |
| 2 | phenyl | -CH(CH₃)CH₂CH(CH₃)₂ |
| 3 | phenyl | phenyl-CH₂-CH(CH₃)- |

TABLE 4-continued (ID)

| No. | A | G |
|---|---|---|
| 4 | 4-methylphenyl | H₃C-CH(CH₃)-CH(CH₃)- |
| 5 | 4-methylphenyl | -CH(CH₃)CH₂CH(CH₃)₂ |
| 6 | 4-methylphenyl | phenyl-CH₂-CH(CH₃)- |
| 7 | 4-methylphenyl | indol-3-yl-CH₂-CH(CH₃)- |
| 8 | 4-pentylphenyl (H₃C-(CH₂)₄-) | phenyl-CH₂-CH(CH₃)- |
| 9 | 3-pyridyl | H₃C-CH(CH₃)-CH(CH₃)- |
| 10 | 3-pyridyl | -CH(CH₃)CH₂CH(CH₃)₂ |
| 11 | 3-pyridyl | phenyl-CH₂-CH(CH₃)- |

TABLE 5

(IE)

Structure: A—NH—C(=O)—NH—[phenyl]—S(=O)₂—NH—G—C(=O)—NH—OH

| No. | A | G |
|-----|---|---|
| 1 | phenyl | isobutyl with CH₃ (isopropyl-methyl) |
| 2 | phenyl | CH(CH₃)CH₂CH(CH₃)₂ |
| 3 | phenyl | CH₂-phenyl-CH(CH₃)₂ (phenylisobutyl) |
| 4 | 4-methylphenyl | isopropyl-methyl |
| 5 | 4-methylphenyl | CH(CH₃)CH₂CH(CH₃)₂ |
| 6 | 4-methylphenyl | phenylisobutyl |
| 7 | 4-methylphenyl | 3-(2-methylpropyl)-1H-indol-yl |
| 8 | 4-(n-pentyl)phenyl [H₃C—(CH₂)₄—] | phenylisobutyl |

TABLE 5-continued (IE)

Structure: A—NH—C(=O)—NH—[phenyl]—S(=O)₂—NH—G—C(=O)—NH—OH

| No. | A | G |
|-----|---|---|
| 9 | pyridin-3-yl | isopropyl-methyl |
| 10 | pyridin-3-yl | CH(CH₃)CH₂CH(CH₃)₂ |
| 11 | pyridin-3-yl | phenylisobutyl |

TABLE 6

(IF)

Structure: A—O—C(=O)—O—[phenyl]—S(=O)₂—NH—G—C(=O)—NH—OH

| No. | A | G |
|-----|---|---|
| 1 | phenyl | isopropyl-methyl |
| 2 | phenyl | CH(CH₃)CH₂CH(CH₃)₂ |
| 3 | phenyl | phenylisobutyl |
| 4 | 4-methylphenyl | isopropyl-methyl |

TABLE 6-continued (IF)

Structure: A—O—C(=O)—O—[phenyl]—S(=O)₂—NH—G—C(=O)—NH—OH

| No. | A | G |
|-----|---|---|
| 5 | 4-methylphenyl (H₃C-C₆H₄-) | -CH(CH₂CH(CH₃)₂)(CH₃) (with extra CH₃) |
| 6 | 4-methylphenyl | -CH₂CH(CH₃)₂ with phenyl (phenylisobutyl) |
| 7 | 4-methylphenyl | 3-(1H-indolyl)-2-methylpropyl |
| 8 | 4-pentylphenyl (H₃C-(CH₂)₄-C₆H₄-) | phenylisobutyl |
| 9 | pyridin-3-yl | -CH(CH(CH₃)₂)(CH₃) |
| 10 | pyridin-3-yl | -CH(CH₃)CH₂CH(CH₃)₂ with CH₃ |
| 11 | pyridin-3-yl | phenylisobutyl |

TABLE 7

(IG)

Structure: A—O—C(=O)—O—[phenyl]—S(=O)₂—NH—G—C(=O)—NH—OH

| No. | A | G |
|-----|---|---|
| 1 | phenyl | -CH(CH(CH₃)₂)(CH₃) |
| 2 | phenyl | -CH(CH₃)CH₂CH(CH₃)₂ |
| 3 | phenyl | phenylisobutyl |
| 4 | 4-methylphenyl | -CH(CH(CH₃)₂)(CH₃) |
| 5 | 4-methylphenyl | -CH(CH₃)CH₂CH(CH₃)₂ |
| 6 | 4-methylphenyl | phenylisobutyl |
| 7 | 4-methylphenyl | 3-(1H-indolyl)-2-methylpropyl |
| 8 | 4-pentylphenyl (H₃C-(CH₂)₄-C₆H₄-) | phenylisobutyl |

TABLE 7-continued (IG)

| No. | A | G |
|---|---|---|
| 9 | 3-pyridyl | isopropyl-methyl (H₃C-CH(CH₃)-CH(CH₃)-) |
| 10 | 3-pyridyl | CH(CH₃)-CH₂-CH(CH₃)₂ |
| 11 | 3-pyridyl | CH₂-CH(CH₃)-phenyl (benzyl-isobutyl) |

TABLE 8

(IH)

| No. | A | G |
|---|---|---|
| 1 | phenyl | H₃C-CH(CH₃)-CH(CH₃)- |
| 2 | phenyl | CH(CH₃)-CH₂-CH(CH₃)₂ |
| 3 | phenyl | CH₂-CH(CH₃)-phenyl |
| 4 | 4-methylphenyl | H₃C-CH(CH₃)-CH(CH₃)- |

TABLE 8-continued (IH)

| No. | A | G |
|---|---|---|
| 5 | 4-methylphenyl | phenyl-CH₂-CH(CH₃)₂ |
| 6 | 4-methylphenyl | phenyl-CH₂-CH(CH₃)₂ |
| 7 | 4-methylphenyl | indol-3-yl-CH₂-CH(CH₃)₂ |
| 8 | 4-pentylphenyl (H₃C-(CH₂)₄-) | phenyl-CH₂-CH(CH₃)₂ |
| 9 | 3-pyridyl | H₃C-CH(CH₃)-CH(CH₃)- |
| 10 | 3-pyridyl | CH(CH₃)-CH₂-CH(CH₃)₂ |
| 11 | 3-pyridyl | phenyl-CH₂-CH(CH₃)₂ |

TABLE 9

(IJ)

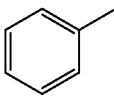

| No. | A | G |
|---|---|---|
| 1 | phenyl | isopropyl-methyl (H₃C–CH(CH₃)–) |
| 2 | phenyl | isobutyl-methyl |
| 3 | phenyl | 2-methylpropyl-phenyl (benzyl-isobutyl) |
| 4 | 4-methylphenyl | isopropyl-methyl |
| 5 | 4-methylphenyl | isobutyl-methyl |
| 6 | 4-methylphenyl | 2-methylpropyl-phenyl |
| 7 | 4-methylphenyl | 1H-indol-3-ylmethyl-isobutyl |
| 8 | 4-pentylphenyl (H₃C–(CH₂)₄–C₆H₄–) | 2-methylpropyl-phenyl |

TABLE 9-continued (IJ)

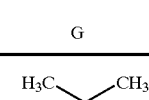

| No. | A | G |
|---|---|---|
| 9 | pyridin-3-yl | isopropyl-methyl |
| 10 | pyridin-3-yl | isobutyl-methyl |
| 11 | pyridin-3-yl | 2-methylpropyl-phenyl |

TABLE 10

(IK)

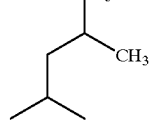

| No. | A | G |
|---|---|---|
| 1 | phenyl | isopropyl-methyl |
| 2 | phenyl | isobutyl-methyl |
| 3 | phenyl | 2-methylpropyl-phenyl |

TABLE 10-continued
(IK)
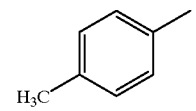
| No. | A | G |
|---|---|---|
| 4 | 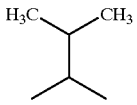 | 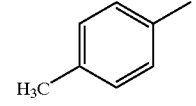 |
| 5 | 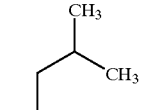 | 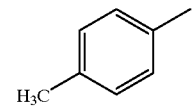 |
| 6 | 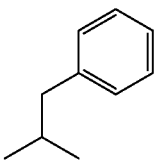 | 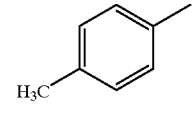 |
| 7 | 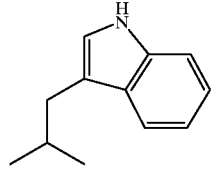 | 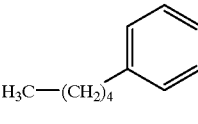 |
| 8 | 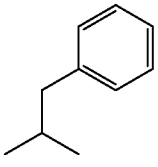 | 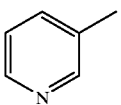 |
| 9 | 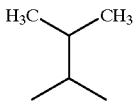 | 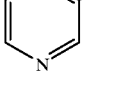 |
| 10 | 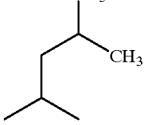 | 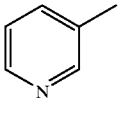 |
| 11 | 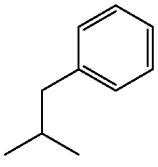 | 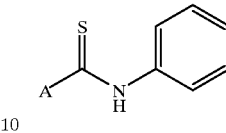 |
TABLE 11
(IL)
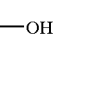
| No. | A | G |
|---|---|---|
| 1 | 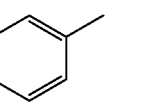 | 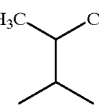 |
| 2 | 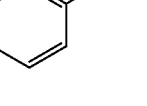 | 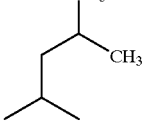 |
| 3 | 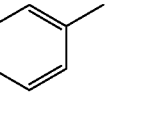 | 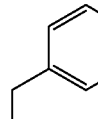 |
| 4 | 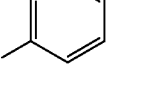 |  |
| 5 | 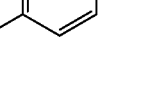 | 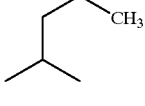 |
| 6 | 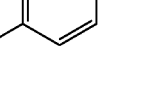 | 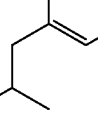 |
| 7 | 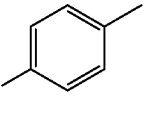 | 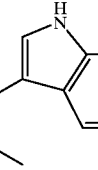 |
| 8 | 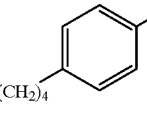 | 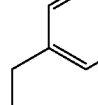 |

TABLE 11-continued (IL)

| No. | A | G |
|---|---|---|
| 9 | 3-pyridyl | isopropyl-CH-CH₃ (3-methylbutan-2-yl) |
| 10 | 3-pyridyl | 4-methylpentan-2-yl |
| 11 | 3-pyridyl | 2-phenylpropyl (isobutylbenzene type) |

TABLE 12

(IM)

| No. | A | G |
|---|---|---|
| 1 | phenyl | 3-methylbutan-2-yl |
| 2 | phenyl | 4-methylpentan-2-yl |
| 3 | phenyl | 2-phenylpropyl |
| 4 | 4-methylphenyl | 3-methylbutan-2-yl |
| 5 | 4-methylphenyl | 4-methylpentan-2-yl |
| 6 | 4-methylphenyl | 2-phenylpropyl |
| 7 | 4-methylphenyl | 3-(1H-indol-3-yl)-2-methylpropyl |
| 8 | 4-pentylphenyl (H₃C—(CH₂)₄—) | 2-phenylpropyl |
| 9 | 3-pyridyl | 3-methylbutan-2-yl |
| 10 | 3-pyridyl | 4-methylpentan-2-yl |
| 11 | 3-pyridyl | 2-phenylpropyl |

TABLE 13

(IN)

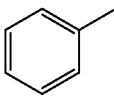

| No. | A | G |
|---|---|---|
| 1 | phenyl | isopropyl-CH(CH₃)₂ variant (H₃C-CH-CH₃) |
| 2 | phenyl | isobutyl branched (CH(CH₃)CH₂CH(CH₃)₂) |
| 3 | phenyl | benzyl-isobutyl (PhCH₂CH(CH₃)—) |
| 4 | 4-methylphenyl | H₃C-CH-CH₃ |
| 5 | 4-methylphenyl | CH(CH₃)CH₂CH(CH₃)₂ |
| 6 | 4-methylphenyl | PhCH₂CH(CH₃)— |
| 7 | 4-methylphenyl | 3-indolylmethyl-isobutyl |
| 8 | 4-(n-pentyl)phenyl [H₃C-(CH₂)₄—] | PhCH₂CH(CH₃)— |

TABLE 13-continued (IN)

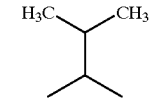

| No. | A | G |
|---|---|---|
| 9 | 3-pyridyl | H₃C-CH-CH₃ |
| 10 | 3-pyridyl | CH(CH₃)CH₂CH(CH₃)₂ |
| 11 | 3-pyridyl | PhCH₂CH(CH₃)— |

TABLE 14

(IP)

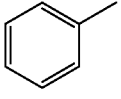

| No. | A | G |
|---|---|---|
| 1 | phenyl | H₃C-CH-CH₃ |
| 2 | phenyl | CH(CH₃)CH₂CH(CH₃)₂ |
| 3 | phenyl | PhCH₂CH(CH₃)— |

TABLE 14-continued (IP)

Structure: A—O—C(=S)—C6H4—SO2—NH—G—C(=O)—NH—OH

| No. | A | G |
|---|---|---|
| 4 | 4-methylphenyl | isopropyl-CH(CH3)- (H3C-CH(CH3)-CH(CH3)-) |
| 5 | 4-methylphenyl | -CH(CH3)-CH2-CH(CH3)2 |
| 6 | 4-methylphenyl | -CH2-CH(CH3)-CH2-phenyl (benzyl isobutyl) |
| 7 | 4-methylphenyl | -CH2-CH(CH3)-indol-3-yl |
| 8 | 4-pentylphenyl (H3C-(CH2)4-C6H4-) | -CH2-CH(CH3)-CH2-phenyl |
| 9 | pyridin-3-yl | H3C-CH(CH3)-CH(CH3)- |
| 10 | pyridin-3-yl | -CH(CH3)-CH2-CH(CH3)2 |
| 11 | pyridin-3-yl | -CH2-CH(CH3)-CH2-phenyl |

TABLE 15

(IQ)

Structure: A—NH—C(=S)—NH—C6H4—SO2—NH—G—C(=O)—NH—OH

| No. | A | G |
|---|---|---|
| 1 | phenyl | H3C-CH(CH3)-CH(CH3)- |
| 2 | phenyl | -CH(CH3)-CH2-CH(CH3)2 |
| 3 | phenyl | -CH2-CH(CH3)-CH2-phenyl |
| 4 | 4-methylphenyl | H3C-CH(CH3)-CH(CH3)- |
| 5 | 4-methylphenyl | -CH(CH3)-CH2-CH(CH3)2 |
| 6 | 4-methylphenyl | -CH2-CH(CH3)-CH2-phenyl |
| 7 | 4-methylphenyl | -CH2-CH(CH3)-indol-3-yl |
| 8 | 4-pentylphenyl (H3C-(CH2)4-C6H4-) | -CH2-CH(CH3)-CH2-phenyl |

TABLE 15-continued (IQ)

[Structure: A-NH-C(=S)-NH-C6H4-SO2-NH-G-C(=O)-NH-OH]

| No. | A | G |
|-----|---|---|
| 9 | 3-pyridyl | -CH(CH3)-CH(CH3)2 |
| 10 | 3-pyridyl | -CH2-CH(CH3)-CH2-CH(CH3)2 (methyl branched) |
| 11 | 3-pyridyl | -CH2-CH(CH3)-CH2-C6H5 (benzyl isobutyl) |

TABLE 16

(IR)

[Structure: A-O-C(=S)-O-C6H4-SO2-NH-G-C(=O)-NH-OH]

| No. | A | G |
|-----|---|---|
| 1 | phenyl | H3C-CH(CH3)-CH(CH3)- |
| 2 | phenyl | -CH2-CH(CH3)-CH2-CH(CH3)2 |
| 3 | phenyl | -CH2-CH(CH3)-CH2-C6H5 |
| 4 | 4-methylphenyl (H3C-C6H4-) | H3C-CH(CH3)-CH(CH3)- |
| 5 | 4-methylphenyl | -CH2-CH(CH3)-CH2-CH3 (isobutyl type) |
| 6 | 4-methylphenyl | -CH2-CH(CH3)-CH2-C6H5 |
| 7 | 4-methylphenyl | indol-3-ylmethyl-CH(CH2-isobutyl) |
| 8 | H3C-(CH2)4-C6H4- | -CH2-CH(CH3)-CH2-C6H5 |
| 9 | 3-pyridyl | H3C-CH(CH3)-CH(CH3)- |
| 10 | 3-pyridyl | -CH2-CH(CH3)-CH(CH3)2 |
| 11 | 3-pyridyl | -CH2-CH(CH3)-CH2-C6H5 |

TABLE 17
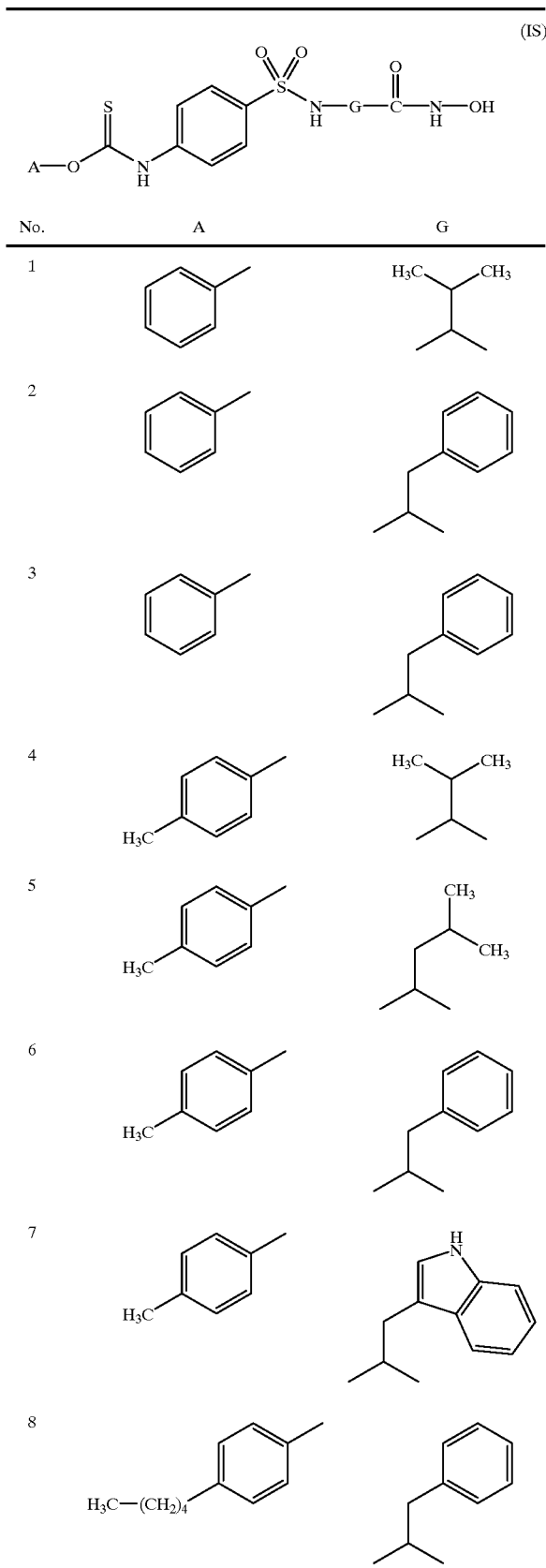
TABLE 17-continued
TABLE 18
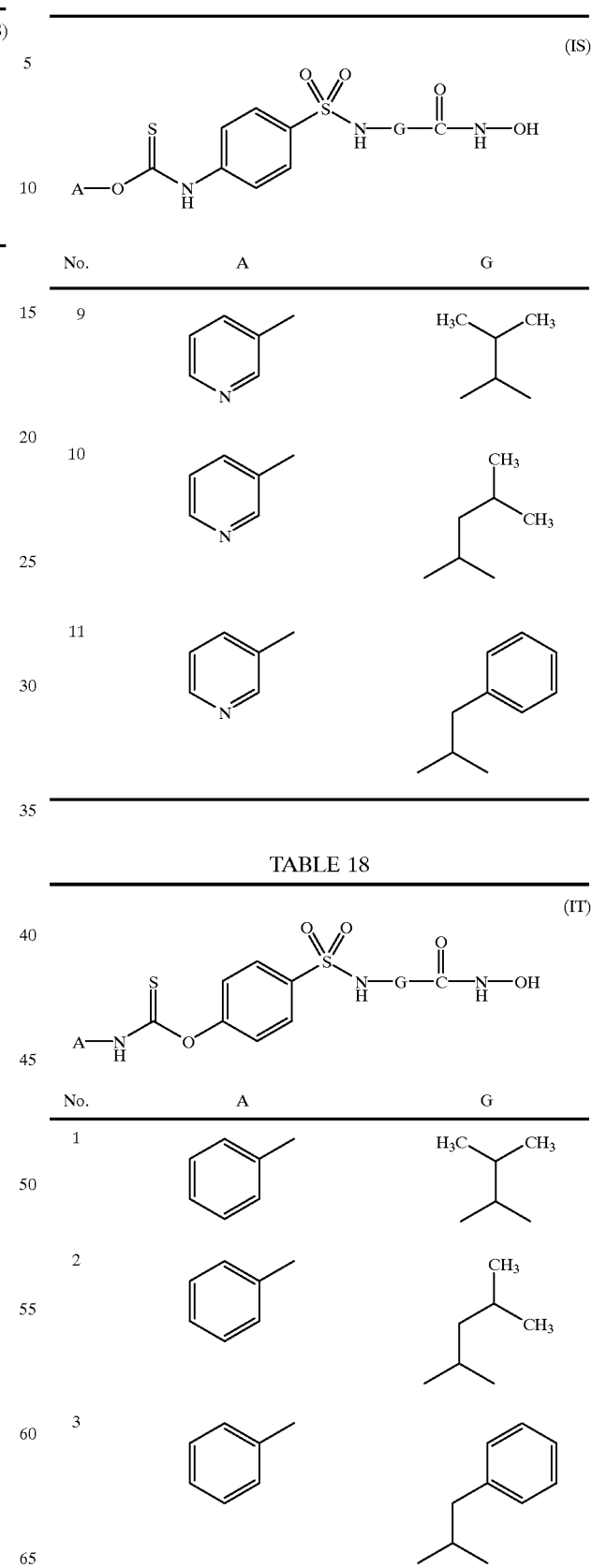

TABLE 18-continued (IT)

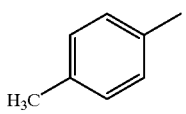

| No. | A | G |
|---|---|---|
| 4 | 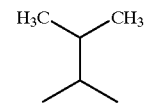 | 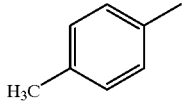 |
| 5 | 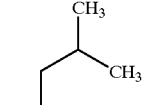 | 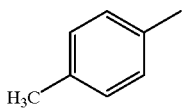 |
| 6 | 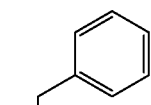 | 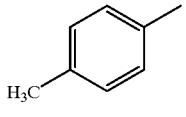 |
| 7 | 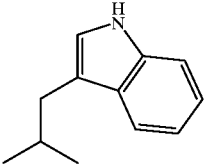 | 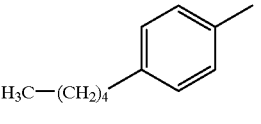 |
| 8 | 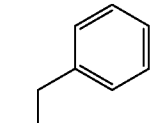 | 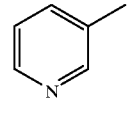 |
| 9 | 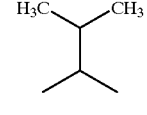 | 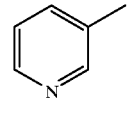 |
| 10 | 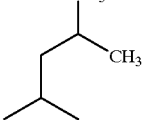 | 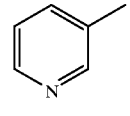 |
| 11 | 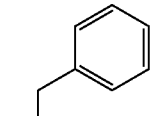 | 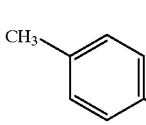 |

TABLE 19

(IU)

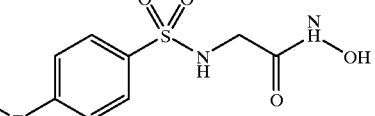

| NO. | E | $R^1$ |
|---|---|---|
| 1 | —CO—NH— | $CH_3$ |
| 2 | —CO—NH— | $CH(CH_3)_2$ |
| 3 | —NH—CO— | $CH_3$ |
| 4 | —NH—CO— | $CH(CH_3)_2$ |
| 5 | —CO—O— | $CH_3$ |
| 6 | —CO—O— | $CH(CH_3)_2$ |
| 7 | —O—CO— | $CH_3$ |
| 8 | —O—CO— | $CH(CH_3)_2$ |
| 9 | —NH—CO—NH— | $CH_3$ |
| 10 | —NH—CO—NH— | $CH(CH_3)_2$ |
| 11 | —O—CO—O— | $CH_3$ |
| 12 | —O—CO—O— | $CH(CH_3)_2$ |
| 13 | —O—CO—NH— | $CH_3$ |
| 14 | —O—CO—NH— | $CH(CH_3)_2$ |
| 15 | —NH—CO—O— | $CH_3$ |
| 16 | —NH—CO—O— | $CH(CH_3)_2$ |
| 17 | —CO—$CH_2$— | $CH_3$ |
| 18 | —CO—$CH_2$— | $CH(CH_3)_2$ |
| 19 | —CO— | $CH_3$ |
| 20 | —CO— | $CH(CH_3)_2$ |
| 21 | —CS—NH— | $CH_3$ |
| 22 | —CS—NH— | $CH(CH_3)_2$ |
| 23 | —NH—CS— | $CH_3$ |
| 24 | —NH—CS— | $CH(CH_3)_2$ |
| 25 | —CS—O— | $CH_3$ |
| 26 | —CS—O— | $CH(CH_3)_2$ |
| 27 | —O—CS— | $CH_3$ |
| 28 | —O—CS— | $CH(CH_3)_2$ |
| 29 | —NH—CS—NH— | $CH_3$ |
| 30 | —NH—CS—NH— | $CH(CH_3)_2$ |
| 31 | —O—CS—O— | $CH_3$ |
| 32 | —O—CS—O— | $CH(CH_3)_2$ |
| 33 | —O—CS—NH— | $CH_3$ |
| 34 | —O—CS—NH— | $CH(CH_3)_2$ |
| 35 | —NH—CS—O— | $CH_3$ |
| 36 | —NH—CS—O— | $CH(CH_3)_2$ |

TABLE 20

(IW)

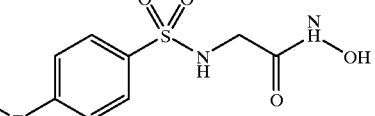

| NO. | E | $R^1$ |
|---|---|---|
| 1 | —CO—NH— | $CH_3$ |
| 2 | —CO—NH— | $CH(CH_3)_2$ |
| 3 | —NH—CO— | $CH_3$ |
| 4 | —NH—CO— | $CH(CH_3)_2$ |
| 5 | —CO—O— | $CH_3$ |
| 6 | —CO—O— | $CH(CH_3)_2$ |
| 7 | —O—CO— | $CH_3$ |
| 8 | —O—CO— | $CH(CH_3)_2$ |
| 9 | —NH—CO—NH— | $CH_3$ |
| 10 | —NH—CO—NH— | $CH(CH_3)_2$ |
| 11 | —O—CO—O— | $CH_3$ |

TABLE 20-continued (IW)

| NO. | E | R¹ |
|---|---|---|
| 12 | —O—CO—O— | CH(CH$_3$)$_2$ |
| 13 | —O—CO—NH— | CH$_3$ |
| 14 | —O—CO—NH— | CH(CH$_3$)$_2$ |
| 15 | —NH—CO—O— | CH$_3$ |
| 16 | —NH—CO—O— | CH(CH$_3$)$_2$ |
| 17 | —CO—CH$_2$— | CH$_3$ |
| 18 | —CO—CH$_2$— | CH(CH$_3$)$_2$ |
| 19 | —CO— | CH$_3$ |
| 20 | —CO— | CH(CH$_3$)$_2$ |
| 21 | —CS—NH— | CH$_3$ |
| 22 | —CS—NH— | CH(CH$_3$)$_2$ |
| 23 | —NH—CS— | CH$_3$ |
| 24 | —NH—CS— | CH(CH$_3$)$_2$ |
| 25 | —CS—O— | CH$_3$ |
| 26 | —CS—O— | CH(CH$_3$)$_2$ |
| 27 | —O—CS— | CH$_3$ |
| 28 | —O—CS— | CH(CH$_3$)$_2$ |
| 29 | —NH—CS—NH— | CH$_3$ |
| 30 | —NH—CS—NH— | CH(CH$_3$)$_2$ |
| 31 | —O—CS—O— | CH$_3$ |
| 32 | —O—CS—O— | CH(CH$_3$)$_2$ |
| 33 | —O—CS—NH— | CH$_3$ |
| 34 | —O—CS—NH— | CH(CH$_3$)$_2$ |
| 35 | —NH—CS—O— | CH$_3$ |
| 36 | —NH—CS—O— | CH(CH$_3$)$_2$ |

TABLE 21

(IY)

| NO. | E | R¹ |
|---|---|---|
| 1 | —CO—NH— | CH$_3$ |
| 2 | —CO—NH— | CH(CH$_3$)$_2$ |
| 3 | —NH—CO— | CH$_3$ |
| 4 | —NH—CO— | CH(CH$_3$)$_2$ |
| 5 | —CO—O— | CH$_3$ |
| 6 | —CO—O— | CH(CH$_3$)$_2$ |
| 7 | —O—CO— | CH$_3$ |
| 8 | —O—CO— | CH(CH$_3$)$_2$ |
| 9 | —NH—CO—NH— | CH$_3$ |
| 10 | —NH—CO—NH— | CH(CH$_3$)$_2$ |
| 11 | —O—CO—O— | CH$_3$ |
| 12 | —O—CO—O— | CH(CH$_3$)$_2$ |
| 13 | —O—CO—NH— | CH$_3$ |
| 14 | —O—CO—NH— | CH(CH$_3$)$_2$ |
| 15 | —NH—CO—O— | CH$_3$ |
| 16 | —NH—CO—O— | CH(CH$_3$)$_2$ |
| 17 | —CO—CH$_2$— | CH$_3$ |
| 18 | —CO—CH$_2$— | CH(CH$_3$)$_2$ |
| 19 | —CO— | CH$_3$ |
| 20 | —CO— | CH(CH$_3$)$_2$ |
| 21 | —CS—NH— | CH$_3$ |
| 22 | —CS—NH— | CH(CH$_3$)$_2$ |

TABLE 21-continued (IY)

| NO. | E | R¹ |
|---|---|---|
| 23 | —NH—CS— | CH$_3$ |
| 24 | —NH—CS— | CH(CH$_3$)$_2$ |
| 25 | —CS—O— | CH$_3$ |
| 26 | —CS—O— | CH(CH$_3$)$_2$ |
| 27 | —O—CS— | CH$_3$ |
| 28 | —O—CS— | CH(CH$_3$)$_2$ |
| 29 | —NH—CS—NH— | CH$_3$ |
| 30 | —NH—CS—NH— | CH(CH$_3$)$_2$ |
| 31 | —O—CS—O— | CH$_3$ |
| 32 | —O—CS—O— | CH(CH$_3$)$_2$ |
| 33 | —O—CS—NH— | CH$_3$ |
| 34 | —O—CS—NH— | CH(CH$_3$)$_2$ |
| 35 | —NH—CS—O— | CH$_3$ |
| 36 | —NH—CS—O— | CH(CH$_3$)$_2$ |

TABLE 22

(IZ)

| NO. | E | R¹ |
|---|---|---|
| 1 | —CO—NH— | CH$_3$ |
| 2 | —CO—NH— | CH(CH$_3$)$_2$ |
| 3 | —NH—CO— | CH$_3$ |
| 4 | —NH—CO— | CH(CH$_3$)$_2$ |
| 5 | —CO—O— | CH$_3$ |
| 6 | —CO—O— | CH(CH$_3$)$_2$ |
| 7 | —O—CO— | CH$_3$ |
| 8 | —O—CO— | CH(CH$_3$)$_2$ |
| 9 | —NH—CO—NH— | CH$_3$ |
| 10 | —NH—CO—NH— | CH(CH$_3$)$_2$ |
| 11 | —O—CO—O— | CH$_3$ |
| 12 | —O—CO—O— | CH(CH$_3$)$_2$ |
| 13 | —O—CO—NH— | CH$_3$ |
| 14 | —O—CO—NH— | CH(CH$_3$)$_2$ |
| 15 | —NH—CO—O— | CH$_3$ |
| 16 | —NH—CO—O— | CH(CH$_3$)$_2$ |
| 17 | —CO—CH$_2$— | CH$_3$ |
| 18 | —CO—CH$_2$— | CH(CH$_3$)$_2$ |
| 19 | —CO— | CH$_3$ |
| 20 | —CO— | CH(CH$_3$)$_2$ |
| 21 | —CS—NH— | CH$_3$ |
| 22 | —CS—NH— | CH(CH$_3$)$_2$ |
| 23 | —NH—CS— | CH$_3$ |
| 24 | —NH—CS— | CH(CH$_3$)$_2$ |
| 25 | —CS—O— | CH$_3$ |
| 26 | —CS—O— | CH(CH$_3$)$_2$ |
| 27 | —O—CS— | CH$_3$ |
| 28 | —O—CS— | CH(CH$_3$)$_2$ |
| 29 | —NH—CS—NH— | CH$_3$ |
| 30 | —NH—CS—NH— | CH(CH$_3$)$_2$ |
| 31 | —O—CS—O— | CH$_3$ |
| 32 | —O—CS—O— | CH(CH$_3$)$_2$ |
| 33 | —O—CS—NH— | CH$_3$ |

TABLE 22-continued

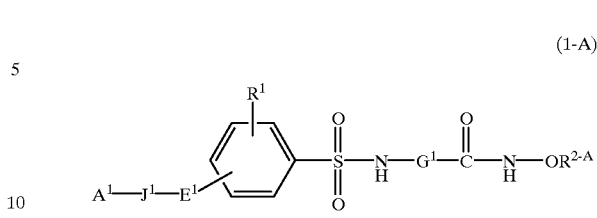

(IZ)

| NO. | E | R¹ |
|---|---|---|
| 34 | —O—CS—NH— | CH(CH₃)₂ |
| 35 | —NH—CS—O— | CH₃ |
| 36 | —NH—CS—O— | CH(CH₃)₂ |

TABLE 23

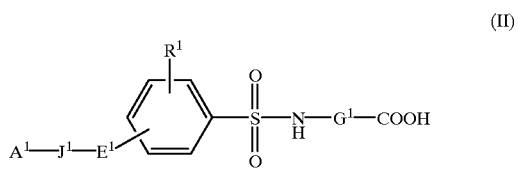

(IAA)

| NO. | E | R¹ |
|---|---|---|
| 1 | —CO—NH— | CH₃ |
| 2 | —CO—NH— | CH(CH₃)₂ |
| 3 | —NH—CO— | CH₃ |
| 4 | —NH—CO— | CH(CH₃)₂ |
| 5 | —CO—O— | CH₃ |
| 6 | —CO—O— | CH(CH₃)₂ |
| 7 | —O—CO— | CH₃ |
| 8 | —O—CO— | CH(CH₃)₂ |
| 9 | —NH—CO—NH— | CH₃ |
| 10 | —NH—CO—NH— | CH(CH₃)₂ |
| 11 | —O—CO—O— | CH₃ |
| 12 | —O—CO—O— | CH(CH₃)₂ |
| 13 | —O—CO—NH— | CH₃ |
| 14 | —O—CO—NH— | CH(CH₃)₂ |
| 15 | —NH—CO—O— | CH₃ |
| 16 | —NH—CO—O— | CH(CH₃)₂ |
| 17 | —CO—CH₂— | CH₃ |
| 18 | —CO—CH₂— | CH(CH₃)₂ |
| 19 | —CO— | CH₃ |
| 20 | —CO— | CH(CH₃)₂ |
| 21 | —CS—NH— | CH₃ |
| 22 | —CS—NH— | CH(CH₃)₂ |
| 23 | —NH—CS— | CH₃ |
| 24 | —NH—CS— | CH(CH₃)₂ |
| 25 | —CS—O— | CH₃ |
| 26 | —CS—O— | CH(CH₃)₂ |
| 27 | —O—CS— | CH₃ |
| 28 | —O—CS— | CH(CH₃)₂ |
| 29 | —NH—CS—NH— | CH₃ |
| 30 | —NH—CS—NH— | CH(CH₃)₂ |
| 31 | —O—CS—O— | CH₃ |
| 32 | —O—CS—O— | CH(CH₃)₂ |
| 33 | —O—CS—NH— | CH₃ |
| 34 | —O—CS—NH— | CH(CH₃)₂ |
| 35 | —NH—CS—O— | CH₃ |
| 36 | —NH—CS—O— | CH(CH₃)₂ |

Process for the Preparation (A) In the compounds of the present invention of the formula (I), the compound in which $R^2$ is not hydrogen, and A—J—E—, substituents of Ar in A, and $R^6$ and $R^7$ in G are not —COOH, amino, hydroxy or a group containing —COOH, amino or hydroxy, A—J—E— is not —CSOH that is the compound of the formula (I-A):

$$(1-A)$$

wherein $G^1$, $E^1$, $J^1$ and $A^1$ are as hereinbefore defined for G, E, J and A, with the proviso that $A^1$—$J^1$—$E^1$—, substituents of Ar in $A^1$, and $R^6$ and $R^7$ in $G^1$ are not —COOH, amino, hydroxy or a group containing —COOH, amino or hydroxy, $A^1$—$J^1$—$E^1$— is not —CSOH, $R^{2-A}$ is C1–8 alkyl, phenyl, or C1–4 alkyl substituted by phenyl, and the other symbols are as hereinbefore defined;

may be prepared by amidation of a compound of the formula (II):

$$(II)$$

wherein all the symbols are as hereinbefore defined; with a compound of the formula (III):

$$H_2N\text{—}OR^{2-A} \qquad (III)$$

wherein all the symbols are as hereinbefore defined.

The method of amidation is known. It includes the method
(1) via an acyl halide,
(2) via a mixed acid anhydride,
(3) using a condensing agent.

These methods are explained as follows.

(1) The method via an acyl halide, for example, may be carried out in an organic solvent (e.g. chloroform, methylene chloride, diethyl ether or tetrahydrofuran) or without a solvent, using an acid halide (e.g. oxalyl chloride or thionyl chloride) at −20° C. to reflux temperature, and the obtained acyl halide derivative may be reacted with an amine in an organic solvent (e.g. chloroform, methylene chloride, diethyl ether ortetrahydrofuran) in the presence of a tertiary amine (e.g. pyridine, triethyl amine, dimethyl aniline ordimethylaminopyridine) at 0–40° C.

(2) The method via a mixed acid anhydride may be carried out, for example, by reacting a carboxylic acid with an acid halide (e.g. pivaloyl chloride, tosyl chloride, mesyl chloride, ethyl chloroformate or isobutyl chloroformate) in an organic solvent (e.g. chloroform, methylene chloride, diethyl ether or tetrahydrofuran) or without a solvent, in the presence of a tertiary amine (e.g. pyridine, triethylamine, dimethylaniline or dimethylaminopyridine) at −20° C.–40° C., and the obtained mixed acid anhydride derivative may be reacted with a corresponding amine in an organic solvent (e.g. chloroform, methylene chloride, diethyl ether or tetrahydrofuran) at 0–40° C.

(3) The method using a condensing agent (e.g. 1,3-dicyclohexylcarbodiimide (DCC), 1-ethyl-3-[3-(dimethylamino)propyl]carbodiimide (EDC) or 2-chloro-1-methylpyridinium iodide) may be carried out, for example, by reacting a carboxylic acid with an amine in an organic solvent (e.g. chloroform, methylene chloride, dimethylformamide or diethyl ether) or without a solvent, optionally in the presence of a tertiary amine (e.g. pyridine, triethylamine, dimethylaniline or dimethylaminopyridine) using a condensing agent at 0–40° C.

The reactions described in (1), (2) and (3) may be carried out under an inert gas (e.g. argon or nitrogen) to avoid water in order to obtain a preferable result.

(B) In the compounds of the present invention of the formula (I), the compound in which $R^2$ is hydrogen, or at least one of A—J—E—, substituents of Ar in A, and $R^6$ or $R^7$ in G is —COOH, amino, hydroxy or a group containing —COOH, amino or hydroxy, or A—J—E— is —CSOH that is the compound of the formula (I-B):

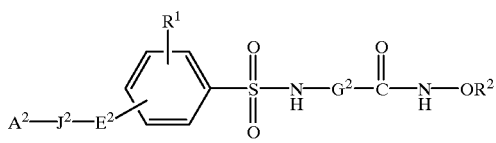

(1-B)

wherein $G^2$, $E^2$, $J^2$ and $A^2$ are as hereinbefore defined for G, E, J and A, with the proviso that at least one of $A^2$—$J^2$—$E^2$—, substituents of Ar in $A^2$, and $R^6$ or $R^7$ in $G^2$ is —COOH, amino, hydroxy or a group containing —COOH, amino or hydroxy, or $A^2$—$J^2$—$E^2$— is —CSOH, or $R^2$ is hydrogen, and the other symbols are as hereinbefore defined;

may be prepared by deprotection under alkaline conditions or acidic conditions, or hydrogenolysis of a compound of the formula (I-A) prepared by the above method.

Deprotection under alkaline conditions, for example, may be carried out in an organic solvent (e.g. methanol, tetrahydrofuran ordioxane), using an alkali metal hydroxide (e.g. potassium hydroxide or sodium hydroxide), an alkaline earth metal hydroxide (e.g. calcium hydroxide), or a carbonate (e.g. sodium carbonate or potassium carbonate.), an aqueous solution thereof or a mixture thereof at 0–40° C.

Deprotection under acidic conditions, for example, may be carried out in a solvent (e.g. methylene chloride, dioxane, ethyl acetate, acetic acid, water or a mixture of two or more thereof), using an organic acid (e.g. trifluoroacetic acid), or an inorganic acid (e.g. hydrogen chloride or hydrogen bromide) or a mixture thereof at 0–120° C.

Hydrogenolysis, for example, may be carried out in a solvent (e.g. tetrahydrofuran, dioxane, dimethoxyethane, diethyl ether, methanol, ethanol, benzene, toluene, dimethylformamide, water, ethyl acetate, acetic acid or a mixture of two or more thereof), in the presence of a catalyst (e.g. palladium on carbon, palladium black, palladium hydroxide, platinum dioxide, Raney-nickel), optionally in the presence of an inorganic acid (e.g. hydrochloric acid, sulfuric acid, hypochlorous acid, boric acid or tetrafluoroboric acid) or an organic acid (e.g. acetic acid, p-toluenesulfonic acid, oxalic acid, trifluoroacetic acid or formic acid), at ordinary or elevated pressure of hydrogen gas or ammonium formate at 0–200° C.

As will be apparent to those skilled in the art, t-butyl or benzyl may be used protecting groups for carboxyl or hydroxy, but other groups which may be removed easily and selectively are also preferred. For example, the groups described in T. W. Greene, Protective Groups in Organic Synthesis, Wiley, New York, 1991, may be used.

Benzyloxycarbonyl or t-butoxycarbonyl may be used as protecting groups for amino, but other groups which may be removed easily and selectively are also preferred.

t-Butyl or benzyl may be used as protecting groups for hydroxamic acid, but other groups which may be removed easily and selectively are also preferred. For example, —C(CH$_3$)$_2$—OCH$_3$ may be used.

The desired compound of the present invention may be easily prepared using these protecting groups.

Besides, the compound of the formula (I-B) may be also prepared by reacting the above compound of the formula (II) with 1,1'-carbonyldiimidazole and hydroxylamine, followed by deprotection, if necessary, e.g. deprotection under alkaline conditions or acidic conditions, or hydrogenolysis.

This type of reaction is known, for example, may be carried out in an organic solvent (e.g. dimethylformamide or tetrahydrofuran), optionally in the presence of an amine (e.g. triethylamine or, pyridine) at 0–40° C.

The compounds of the formula (II) may be prepared according to known methods, methods described in the following schemes 1–7 or methods described in the Examples.

Scheme 1

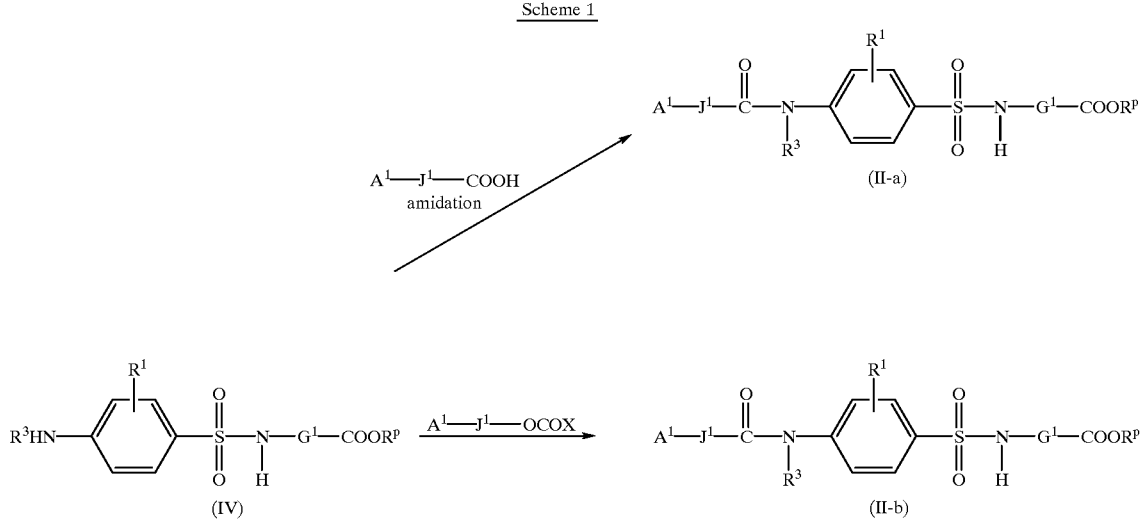

-continued
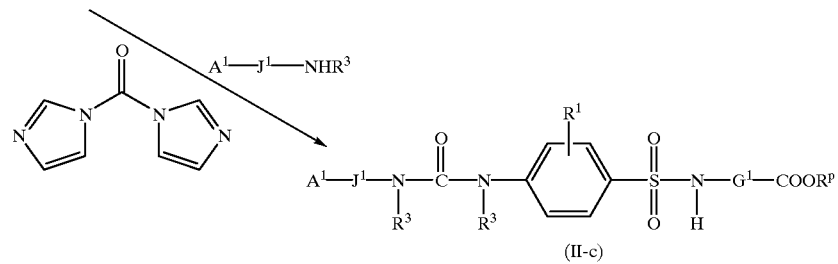
Scheme 2
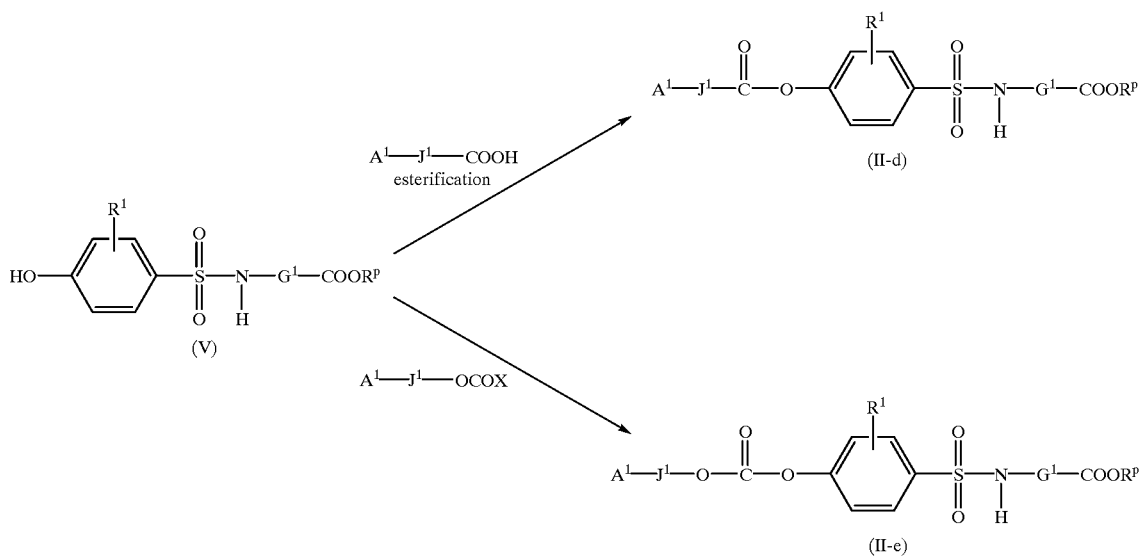
Scheme 3
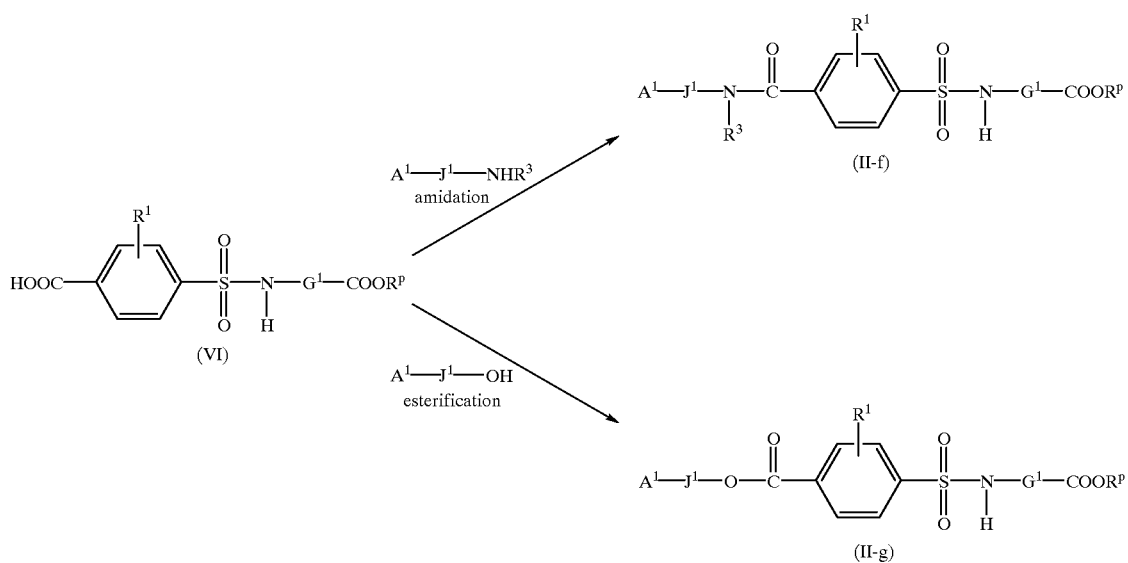

Scheme 4
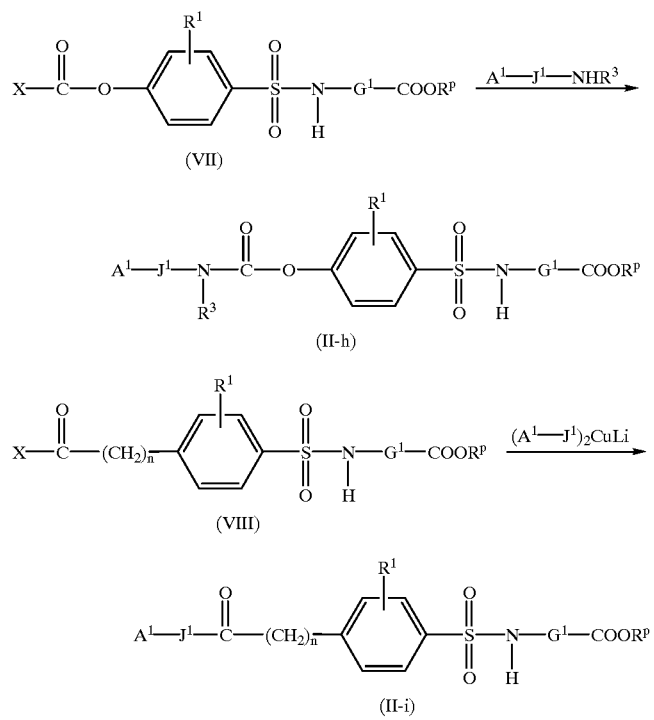
Scheme 5
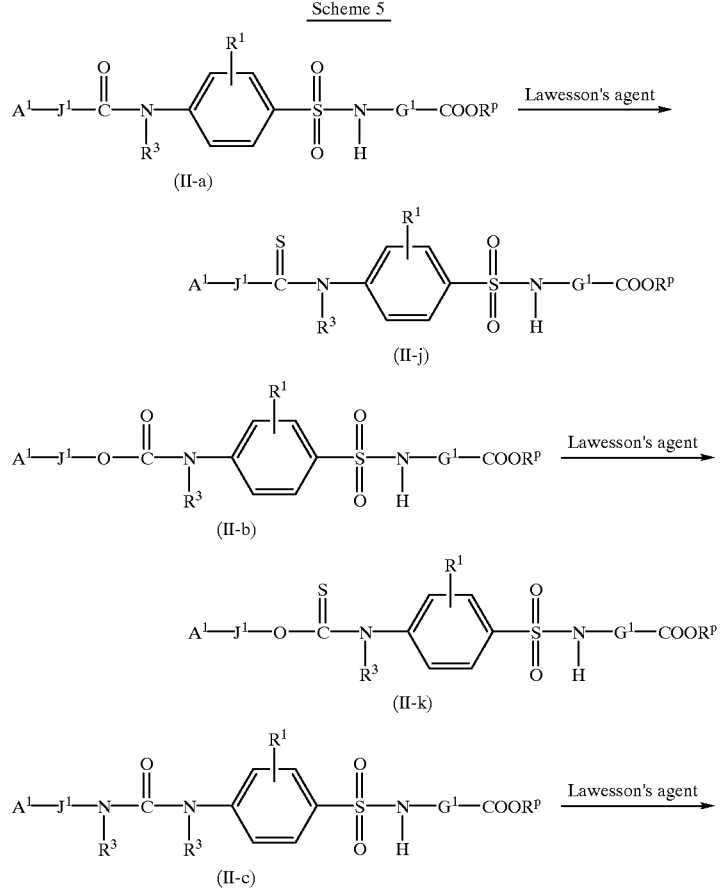

-continued
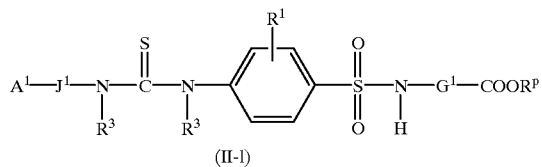
(II-l)
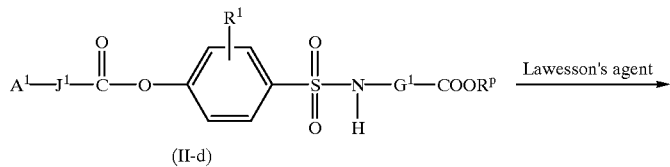
(II-d)
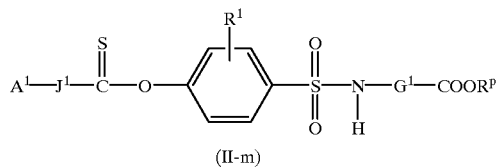
(II-m)
Scheme 6
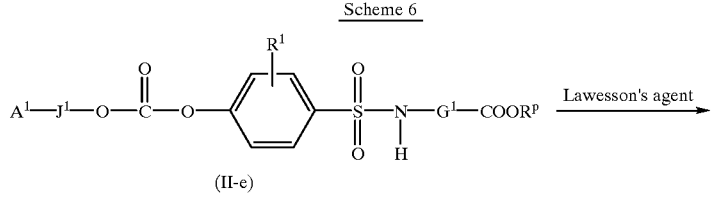
(II-e)
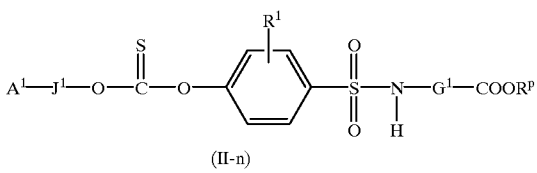
(II-n)
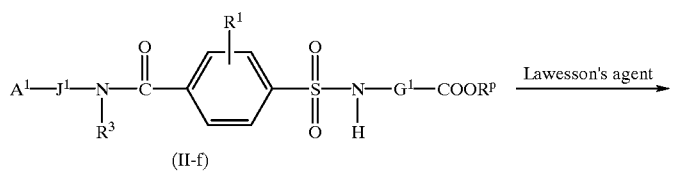
(II-f)
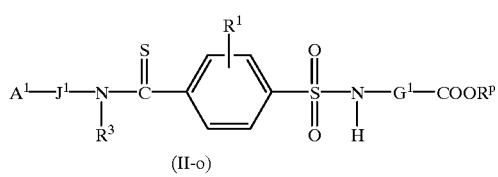
(II-o)
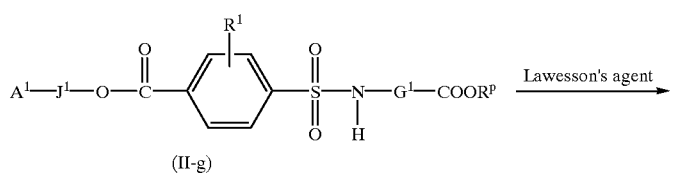
(II-g)
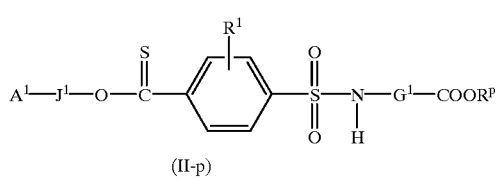
(II-p)

-continued

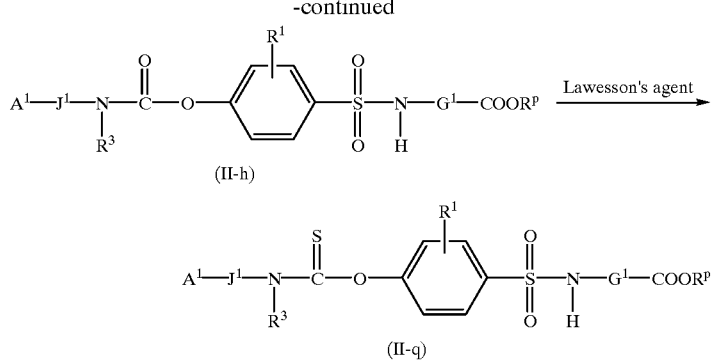

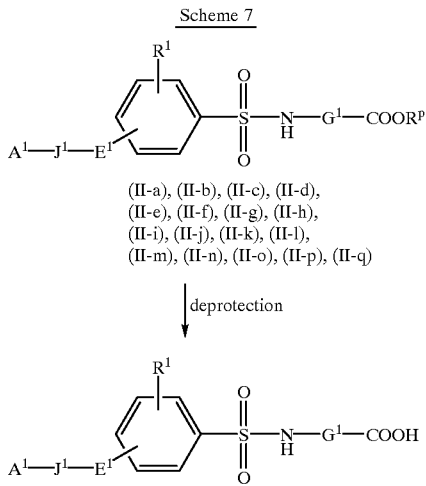

In the above schemes, $R^p$ is a carboxyl-protecting group (e.g. benzyl or t-butyl), n is 0 or 1 and the other symbols are as hereinbefore defined.

Each reaction in the above schemes may be carried out by a known method. In the above schemes, the compounds of the formulae (IV), (V), (VI), (VII) and (VIII) are known per se or may be prepared by known methods.

In each reaction in the present specification, products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

The other starting materials and reagents in the present invention are known per se or may be prepared by known methods.

PHARMACOLOGICAL ACTIVITIES

The potency of inhibitory activity against each matrix metalloproteinase is confirmed as below. The $IC_{50}$ value for inhibition of gelatinase A activity is determined as follows.
(1) Inhibitory activity against gelatinase A Method Progelatinase A (7 μl; in assay buffer (90 μl )) was purified from human normal skin dermal fibroblasts (HNDF). It was activated by the addition of 10 mM of p-aminophenylmercuric acetate (APMA) (10 μl) for 1 hour at 37° C.

The solution of activated gelatinase A (7 μl tube, 98μl) was mixed with various concentrations of the test compound or dimethylsulfoxide (2 μl) and gelatin (100 μl) labeled with 0.05% fluorescein isothiocyanate (FITC) and incubated for 2 hours at 37° C. The reaction was terminated by the addition of 0.1 M Tris-HCI (pH9.5) containing 94.7% ethanol (750 μl). The mixture was stirred and then allowed to stand for 30 minutes at 0° C. The mixture was centrifuged for 30 minutes at 900×g. The $IC_{50}$ was determined by measuring the fluorescent intensity in the supernatant (Ex= 495 nm, and Em=520 nm). The results are shown in Table 24 (Example number 2 and 2(3)).

Alternatively the inhibitory activity of the test compound was measured by using the synthetic substrate (MOCAc-Pro-Leu-Gly-Leu-$A_2$pr(Dnp)-Ala-Arg-$NH_2$). The substrate solution (890 μl; the final concentration was 13.5 μM) was mixed with various concentrations of the test compound or dimethylsulfoxide (10 ml) for 5 minutes at 37° C. The activated gelatinase A (7 μl/tube, 100 μl) was added to the reaction mixture and further incubated for 20 minutes at 37° C. 0.1 M sodium acetate buffer (2 ml; pH4.0) was added into the mixture. The $IC_{50}$ was determined by measuring the fluorescent intensity (Ex=328 nm, and Em=393 nm) in this solution. The results are shown in Table 24 (Example number 2(4) and 3(2)).

TABLE 24

| Example No. | $IC_{50}$ (μM) |
| --- | --- |
| 2 | 0.0017 |
| 2(3) | 0.0010 |
| 2(4) | 0.00061 |
| 3(2) | 0.00023 |

Toxicity

The toxicity of the compounds of the present invention is very low and therefore, the compounds may be considered safe for pharmaceutical use.

Application for Pharmaceuticals

Inhibition of gelatinases is useful for prevention and/or treatment of diseases induced by overexpression or excess activity of gelatinases, for example, rheumatoid diseases, arthrosteitis, unusual bone resorption, osteoporosis, periodontitis, interstitial nephritis, arteriosclerosis, pulmonary emphysema, cirrhosis, cornea injury, metastasis of, invasion of or growth of tumor cells, autoimmune disease (e.g. Crohn's disease, Sjogren's syndrome), disease caused by vascular emigration or infiltration of leukocytes, arterialization in animals including human beings, especially human beings.

For the purpose above described, the compounds of the formula (I), of the present invention and non-toxic salts thereof (e.g. acid addition salts) or hydrates may be normally by administered systemically or locally, usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered in the form of, for example, solid compositions, liquid compositions or other compositions for oral administration, injections, liniments or suppositories for parenteral administration.

Solid compositions for oral administration include compressed tablets, pills, capsules, dispersible powders, and granules.

Capsules include hard capsules and soft capsules.

In such compositions, one or more of the active compound(s) may be admixed with at least one inert diluent (such as lactose, mannitol, glucose, hydroxypropyl cellulose, microcrystalline cellulose, starch, polyvinylpyrrolidone or magnesium metasilicate aluminate). The compositions may also comprise, as is normal practice, additional substances other than inert diluents: e.g. lubricating agents (such as magnesium stearate), disintegrating agents (such as cellulose calcium glycolate), stabilizing agents, and agents to assist dissolution (such as glutamic acid or aspartic acid).

The tablets or pills may, if desired, be coated with a film of gastric or enteric material (such as sugar, gelatin, hydroxypropyl cellulose or hydroxypropylmethyl cellulose phthalate), or be coated with two or more films. And further, coating may include containment within capsules of absorbable materials such as gelatin.

Liquid compositions for oral administration include pharmaceutically acceptable emulsions, solutions, syrups and elixirs. In such compositions, one or more of the active compound(s) may be contained in an inert diluent(s) commonly used in the art (e.g. purified water or ethanol). Besides inert diluents, such compositions may also comprise adjuvants (such as wetting agents or suspending agents), sweetening agents, flavouring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (such as sodium sulfate), isotonic buffer (such as sodium chloride, sodium citrate or citric acid). For preparation of such spray compositions, for example, the method described in the U.S. Pat. No. 2,868,691 or 3,095,355 may be used.

Injections for parenteral administration include sterile aqueous or non-aqueous solutions, suspensions and emulsions. Aqueous solutions and suspensions may include distilled water for injection or physiological salt solution. Non-aqueous solutions and suspensions may include propylene glycol, polyethylene glycol, vegetable oil such as olive oil, alcohol such as ethanol or POLYSORBATE80 (registered trade mark).

Injections may comprise additional ingredients other than inert diluents: e.g. preserving agents, wetting agents, emulsifying agents, dispersing agents, stabilizing agents, assisting agents such as agents to assist dissolution (e.g. glutamic acid or aspartic acid).

They may be sterilized for example, by filtration through a bacteria-retaining filter, by incorporation of sterilizing agents in the compositions or by irradiation. They may also be manufactured in the form of sterile solid compositions which may be dissolved in sterile water or some other sterile diluent(s) for injection immediately before use.

Other compositions for parenteral administration include liquids for external use, and endermic liniments, ointment, suppositories for rectal administration and pessaries for vaginal administration which comprise one or more of the active compound(s) and may be prepared by methods known per se.

REFERENCE EXAMPLE AND EXAMPLE

The following reference examples and examples illustrate the present invention, but do not limit the present invention.

The solvents in parentheses show the developing or eluting solvents and the ratios of the solvents used are by volume in chromatographic separations or TLC.

The solvents in parentheses in NMR show the solvents used in measurement.

Reference Example 1

N-[(4-Nitrophenyl)sulfonyl]glycine t-butyl ester

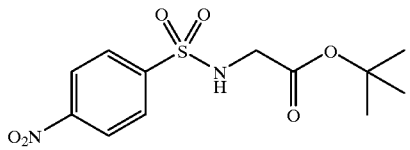

4-Nitrobenzenesulfonyl chloride (46.3 g) was added to a solution of glycine t-butyl ester hydrochloride (35 g) in pyridine (200 ml). The mixture was stirred at room temperature for 1 hour. The reaction mixture was concentrated. The residue was washed with water and then a mixture of hexane and ethyl acetate (9:1) and dried to give the title compound (61.4 g) having the following physical data.

TLC: Rf 0.18 (Hexane: Ethyl acetate=4:1).

Reference Example 2

N-[(4-Aminophenyl)sulfonyl]glycine t-butyl ester

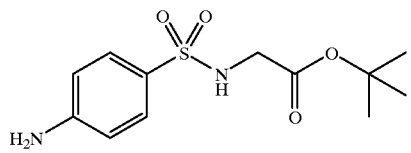

To a solution of the compound prepared in reference example 1 (57.1 g) in ethanol (200 ml) and tetrahydrofuran (200 ml), 10% palladium carbon (2.2 g) was added. The mixture was stirred at room temperature for 3 hours under an atmosphere of hydrogen. The reaction mixture was filtered through celite (registered trade mark). The filtrate was concentrated. The residue was washed with a mixture of hexane and ethyl acetate (4:1) and dried to give the title compound (50 g) having the following physical data.

TLC: Rf 0.36 (Hexane: Ethyl acetate=1:1).

Reference Example 3

N-[[4-(p-Toluoylamino)phenyl]sulfonyl]glycine t-butyl ester

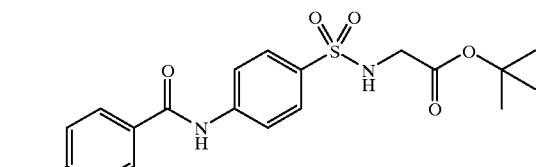

To a solution of the compound prepared in reference example 2 (1.2 g) in pyridine (10 ml), p-toluoyl chloride (0.5 ml) was added at 0° C. The mixture was stirred at room temperature for 30 minutes. To the reaction mixture, 1N hydrochloric acid (100 ml) was added. The mixture was extracted with ethyl acetate. The extract was washed with a saturated aqueous solution of sodium bicarbonate, a saturated aqueous solution of sodium chloride, dried over anhydrous sodium sulfate and concentrated. The residue was washed with ether and dried to give the title compound (1.52 g) having the following physical data.

TLC: Rf 0.56 (Hexane: Ethyl acetate=1:1), NMR (CDCl$_3$): δ 8.08–8.00 (1H, br.s), 7.86 (2H, d, J=9.2 Hz), 7.82 (2H, d, J=9.2 Hz), 7.78 (2H, d, J=8.2 Hz), 7.31 (2H, d, J=8.2 Hz), 5.04 (1H, t, J=5.4 Hz), 3.67 (2H, d, J=5.4 Hz), 2.44 (3H, s), 1.37 (9H, s).

Reference Example 3(1)–3(7)

The compounds having the following physical data were obtained by the same procedure as a series of reactions of reference example 3, using a corresponding compound.

Reference Example 3(1)

N-[[4-(Benzoylamino)phenyl]sulfonyl]glycine t-butyl ester

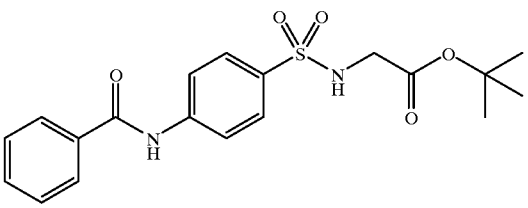

TLC: Rf 0.70 (Ethyl acetate), NMR (CDCl3): δ 8.02 (1H, s), 7.9–7.8 (6H, m), 7.6–7.3 (3H, m), 5.02 (1H, t, J=5.4 Hz), 3.68 (2H, d, J=5.4 Hz), 1.37 (9H, s).

Reference Example 3(2)

N-[[4-(4-Methoxybenzoylamino)phenyl]sulfonyl]glycine t-butyl ester

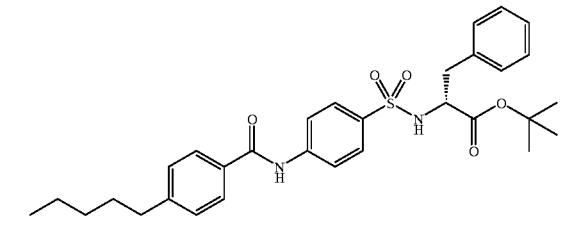

TLC: Rf 0.40 (Hexane: Ethyl acetate=1:1), NMR (CDCl$_3$): δ 7.94–7.90 (1H, br.s), 7.86 (2H, d, J=9.2 Hz), 7.85 (2H, d, J=8.8 Hz), 7.79 (2H, d, J=9.2 Hz), 6.99 (2H, d, J=8.8 Hz), 5.00 (1H, t, J=5.4 Hz), 3.89 (3H, s), 3.67 (2H, d, J=5.4 Hz), 1.37 (9H, s).

Reference Example 3(3)

N-[[4-(4-Pentylbenzoylamino)phenyl]sulfonyl]-D-phenylalanine t-butyl ester

TLC: Rf 0.66 (Hexane: Ethyl acetate=3:2), NMR (CDCl$_3$): δ 7.95 (1H, s), 7.84–7.68 (6H, m), 7.35–7.08 (7H, m), 5.10 (1H, d, J=10.0 Hz), 4.14–4.00 (1H, m), 3.02 (2H, d, J=6.0 Hz), 2.67 (2H, t, J=7.8 Hz), 1.72–1.56 (2H, m), 1.48–1.25 (4H, m), 1.21 (9H, s), 0.89 (3H, t, J=5.0 Hz).

Reference Example 3(4)

N-[[4-(p-Toluoylamino)phenyl]sulfonyl]-D-tryptophan benzyl ester

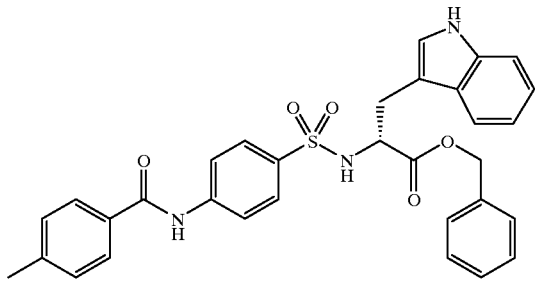

TLC: Rf 0.32 (Hexane: Ethyl acetate=1:1), NMR (CDCl$_3$+CD$_3$OD): δ 7.81 (2H, d, J=8.0 Hz), 7.56 (4H, s), 7.43 (1H, d, J=7.0 Hz), 7.35–7.25 (6H, m), 7.15–7.00 (4H, m), 6.81 (1H, s), 4.92 (2H, s), 4.25 (1H, m), 3.18 (2H, m), 2.45 (3H, s).

Reference Example 3(5)

N-[[3-(Benzoylamino)phenyl]sulfonyl]glycine t-butyl ester

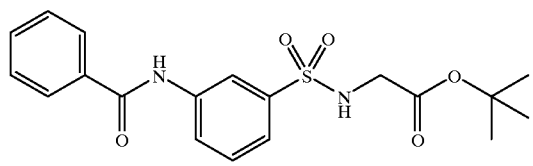

TLC: Rf 0.65 (Hexane: Ethyl acetate=1:1), NMR (CDCl$_3$): δ 8.26–8.16 (2H, m), 8.00 (1H, t, J=1.8 Hz), 7.94–7.87 (2H, m), 7.66–7.46 (5H, m), 5.24 (1H, t, J=5.4 Hz), 3.70 (2H, d, J=5.4 Hz), 1.35 (9H, s).

Reference Example 3(6)

N-[[2-(Benzoylamino)phenyl]sulfonyl]glycine t-butyl ester

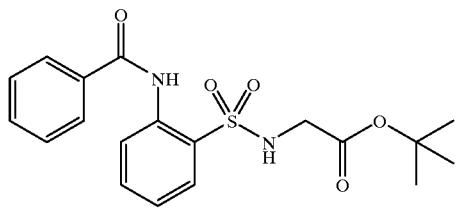

TLC: Rf 0.51 (Hexane: Ethyl acetate=3:2), NMR (CDCl3): δ 10.27 (1H, s), 8.73 (1H, d, J=8.4 Hz), 8.05–7.94 (2H, m), 7.90 (1H, dd, J=1.8 Hz, 8.0 Hz), 7.70–7.45 (4H, m), 7.30–7.18 (1H, m), 5.20 (1H, t, J=5.2 Hz), 3.61 (2H, d, J=5.2 Hz), 1.33 (9H, s).

Reference Example 3(7)

N-[[4-(2-Thienylcarbonylamino)phenyl]sulfonyl]-D-alanine t-butyl ester

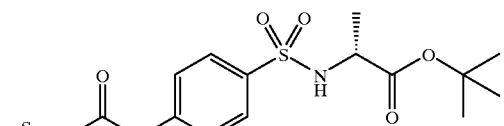

TLC: Rf 0.25 (Hexane: Ethyl acetate=2:1), NMR (DMSO-d6): δ 10.51 (1H, s), 8.12–8.05 (2H, m), 7.94–7.88 (3H, m), 7.74 (2H, d, J=8.8 Hz), 7.24 (1H, t, J=3.8 Hz), 3.72 (1H, quint, J=7.4 Hz), 1.27 (9H, s), 1.14 (3H, d, J=7.4 Hz).

Reference example 4

N-[[4-(p-Toluoylamino)phenyl]sulfonyl]glycine

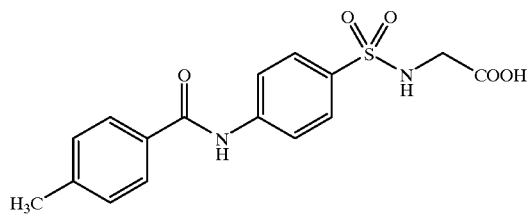

A mixture of the compound prepared in reference example 3 (1.45 g) in trifluoroacetic acid (10 ml) and water (1 ml) was stirred at room temperature for 1 hour. The reaction mixture was concentrated. The residue was washed with ether and dried to give the title compound (1.16 g) having the following physical data.

TLC: Rf0.48 (Chloroform: Methanol: acetic acid= 16:3:1), NMR (DMSO-d6): δ 10.46 (1H, s), 8.02–7.84 (1H), 7.97 (2H, d, J=9.0 Hz), 7.88 (2H, d, J=8.0 Hz), 7.75 (2H, d, J=9.0 Hz), 7.34 (2H, d, J=8.0 Hz), 3.55 (2H, d, J=6.2Hz), 2.40 (3H, s).

Reference Example 4(1)–4(7)

The compounds having the following physical data were obtained by the same procedure as a series of reaction of reference example 4 or by means of a different deprotection method (e.g. hydrogenolysis), using the compound prepared in reference example 3(1)–3(7) instead of the compound prepared in reference example 3.

Reference Example 4(1)

N-[[4-(Benzoylamino)phenyl]sulfonyl]glycine

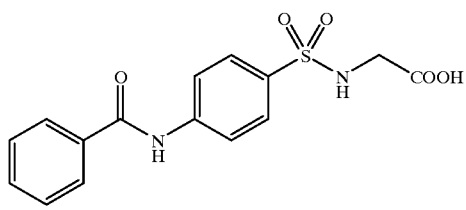

TLC: Rf 0.19 (Chloroform: Methanol: Acetic acid: Water=50:10:1:1), NMR (CD$_3$OD): δ 6 8.0–7.8 (6H, m), 7.6–7.5 (3H, m), 3.70 (2H, s).

Reference Example 4(2)

N-[[4-(4-Methoxybenzoylamino)phenyl]sulfonyl] glycine

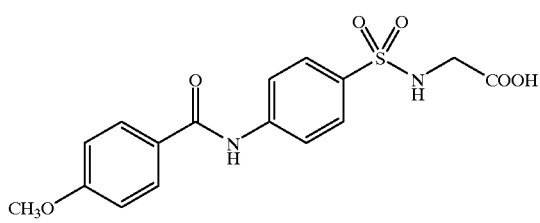

TLC: Rf 0.43 (Chloroform: Methanol: Acetic acid= 16:3:1), NMR (DMSO-d6): δ 10.39 (1H, s), 7.97 (2H, d, J=8.8 Hz), 7.95 (2H, d, J=9.0 Hz), 7.89 (1H, t, J=6.2 Hz), 7.75 (2H, d, J=9.0 Hz), 7.70 (2H, d, J=8.8 Hz), 3.84 (3H, s), 3.55 (2H, d, J=6.2 Hz).

Reference Example 4(3)

N-[[4-(4-Pentylbenzoylamino)phenyl]sulfonyl]-D-phenylalanine

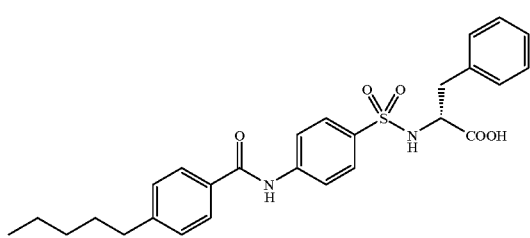

TLC: Rf 0.21 (Chloroform: Methanol: Acetic acid= 95:4:1), NMR (DMSO-d6): δ 13.00–12.20 (1H, br.s), 10.40 (1H, s), 8.11 (1H, d, J=9.0 Hz), 7.88 (2H, d, J=8.6 Hz), 7.84 (2H, d, J=8.4 Hz), 7.52 (2H, d, J=8.6 Hz), 7.34 (2H, d, J=8.4 Hz), 7.28–7.08 (5H, m), 3.92–3.78 (1H, m), 2.93 (1H, dd, J=5.8, 13.4 Hz), 2.71 (1H, dd, J=8.8, 13.4 Hz), 2.66 (2H, t, J=8.2 Hz), 1.70–1.50 (2H, m), 1.44–1.18 (4H, m), 0.87 (3H, t, J=6.8 Hz).

Reference Example 4(4)

N-[[4-(p-Toluoylamino)phenyl]sulfonyl]-D-tryptophan

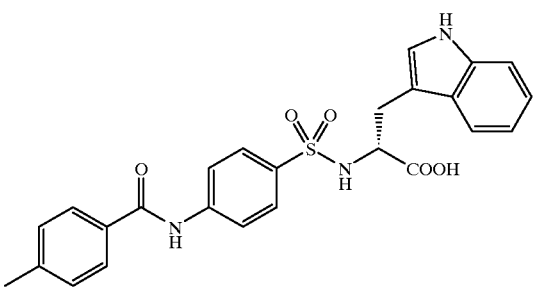

TLC: Rf 0.13 (Chloroform: Methanol: Acetic acid: Water=100:10:1:1), NMR (DMSO-d6): δ 12.57 (1H, br.s), 10.8 (1H, s), 10.42 (1H, s), 8.13 (1H, d, J=8.8 Hz), 7.9–7.8 (4H, m), 7.59 (2H, d, J=8.8 Hz), 7.4–7.25 (4H, m), 7.1–6.9 (3H, m), 3.95–3.85 (1H, m), 3.04 (1H, dd, J=6.0, 18.0 Hz), 2.84 (1H, dd, J=7.4, 18.0 Hz 2.39 (3H, s).

Reference Example 4(5)

N-[[3-(Benzoylamino)phenyl]sulfonyl]glycine

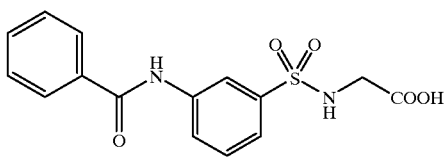

TLC: Rf 0.36 (Chloroform: Methanol: Acetic acid= 16:3:1), NMR (DMSO-d6): δ 10.54 (1H, s), 8.33 (1H, s), 8.14–7.90 (4H, m), 7.68–7.44 (5H, m), 3.60 (2H, d, J=6.0 Hz).

Reference Example 4(6)

N-[[2-(Benzoylamino)phenyl]sulfonyl]glycine

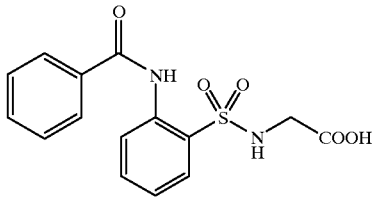

TLC: Rf 0.34 (Chloroform: Methanol: Acetic acid= 90:10:1), NMR (DMSO-d6): δ 13.00–12.60 (1H, br.s), 10.26 (1H, s), 8.67–8.56 (1H), 8.52–8.44 (1H, m), 8.02–7.92 (2H, m), 7.87 (1H, dd, J=1.4, 7.8 Hz), 7.74–7.54 (4H, m), 7.38–7.27 (1H, m), 3.65 (2H, d, J=4.6 Hz).

Reference Example 4(7)

N-[[4-(2-Thienylcarbonylamino)phenyl]sulfonyl]-D-alanine

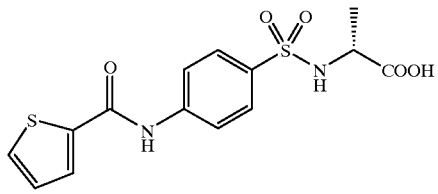

TLC: Rf 0.21 (Chloroform: Methanol: Water=4:1:0.1), NMR (DMSO-d6): δ 12.60 (1H, br.s), 10.49 (1H, s), 8.05–7.98 (2H, m), 7.91–7.85 (3H, m), 7.73 (2H, d, J=8.8 Hz), 7.21 (1H, t, J=3.8 Hz), 3.77–3.68 (1H, m), 1.13 (3H, d, J=7.2 Hz).

Example 1

N-Benzyloxy-N-[N'-[[4-(p-Toluoylamino)phenyl]sulfonyl]glycyl]amide

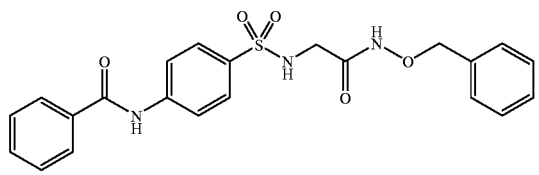

N-Benzylhydroxylamine hydrochloride (192 mg), 1-ethyl-3-[3-(dimethylamino)propyl]carbodiimide (230 mg), 1-hydroxybenzotriazole (199 mg) and triethylamine (0.34 ml) were added, successively, to a solution of the compound prepared in reference example 4 (348 mg) in N,N-dimethylformamide (5 ml). The mixture was stirred at room temperature overnight. The reaction mixture was concentrated. Ethyl acetate was added into the residue. The solution was washed with 1N hydrochloric acid, water, aqueous solution of sodium carbonate, water, successively, dried and concentrated. The residue was washed with ether and dried to give the title compound (417 mg) having the following physical data.

TLC: Rf 0.52 (Chloroform: Methanol: Acetic acid= 9:1:0.5), NMR (DMSO-d6+CC14): δ 11.17 (1H,s), 10.48 (1H,s), 7.98 (2H, d, J=8.8 Hz), 7.87 (2H,d,J=7.8 Hz), 7.76 (2H,d,J=8.8 Hz), 8.1–7.7 (1H,br.s), 7.50–7.25 (7H,m), 4.66 (2H,s), 2.40 (2H,s).

Example 1(1)–1(4)

The compounds having the following physical data were obtained by the same procedure as a series of reactions of example 1, using the Compound prepared in reference example 4(1)–4(4) instead of the compound prepared in reference example 4.

Example 1(1)

N-Benzyloxy-N-[N'-[[4-(benzoylamino)phenyl]sulfonyl]glycol]amide

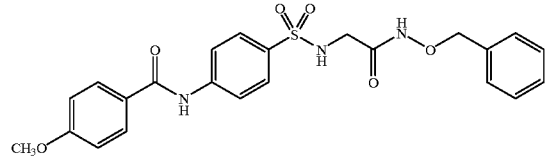

TLC: Rf 0.38 (Chloroform: Methanol: Acetic acid: Water=100:10:1:1), NMR(CDCl$_3$+CD$_3$OD): δ 7.95–7.8 (6H,m), 7.6–7.45 (3H,m), 7.37(5H,s), 4.79 (2H,s), 3.50 (2H,s).

Example 1(2)

N-Benzyloxy-N-[N'-[[4-(4-methoxybenzoylamino)]sulfonyl]glycyl]amide

TLC: Rf 0.52 (Chloroform: Methanol=9:1), NMR (d6-DMSO): δ 11.17 (1H, s), 10.41 (1H, s), 8.04–7.84 (1H), 7.97 (2H, d, J=8.8 Hz), 7.95 (2H, d, J=8.8 Hz), 7.75 (2H, d, J=8.8 Hz), 7.42–7.28 (5H, m), 7.07 (2H, d, J=8.8 Hz), 4.66 (2H, s), 3.84 (3H, s), 3.40–3.30 (2H).

Example 1(3)

N-Benzyloxy-N-[N'-[[4-(4-pentylbenzoylamino)phenyl]sulfonyl]-D-phenylalanyl]amide

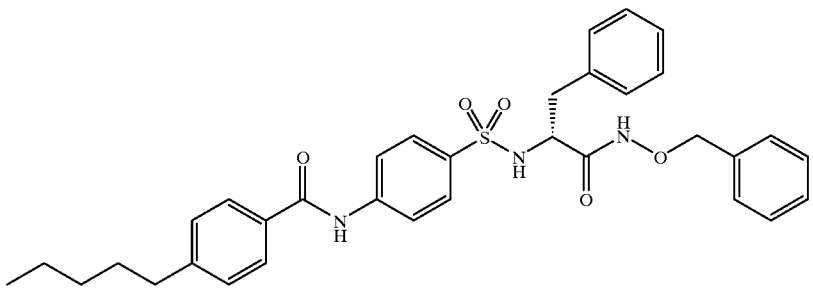

TLC: Rf 0.54 (Chloroform: Methanol=19:1), NMR (DMSO-d6): δ 11.21 (1H, s), 10.43 (1H, s), 8.23 (1H, d, J=9.0 Hz), 7.89 (2H, d, J=8.8 Hz), 7.83 (2H, d, J=8.4 Hz), 7.62 (2H, d, J=8.8 Hz), 7.40–7.08 (12H, m), 4.41 (1H, d, J=11.0 Hz), 4.34 (1H, d, J=11.0 Hz), 3.85–3.68 (1H, m), 2.79 (1H, dd, J=6.8, 13.6 Hz), 2.73–2.60 (1H), 2.65 (2H, t, J=8.2 Hz), 1.70–1.50 (2H, m), 1.45–1.20 (4H, m), 0.86 (3H, t, J=6.6 Hz).

Example 1(4)

N-Benzyloxy-N-[N'-[[4-(p-toluoylamino)phenyl]sulfonyl]-D-tryptophyl]amide

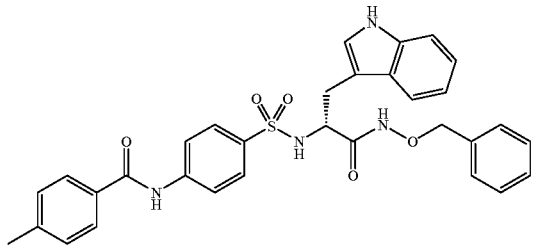

TLC: Rf 0.36 (Chloroform: Methanol=9:1), NMR (DMSO-d6): δ 11.19 (1H, s), 10.80 (1H, s), 10.41 (1H, s),8.16 (1H, d, J=8.2 Hz), 7.84 (4H, m), 7.65 (2H, d, J=8.8 Hz), 7.36–6.92 (12H, m), 4.39 (1H, d, J=13.9 Hz), 4.30 (1H, d, J=13.9 Hz), 3.78 (1H, q, J=8.2 Hz), 3.05–2.70 (2H, m), 2.40 (3H, s).

Example 2

N N-Hydroxy-N-[N'-[[4-(p-toluoylamino)phenyl]sulfonyl]glycyl]amide

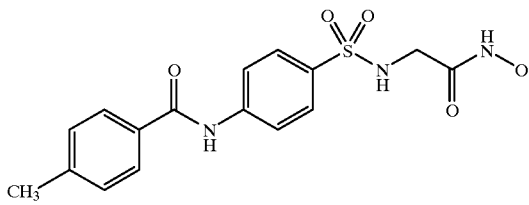

10% Palladium carbon (30 mg) was added to a solution of the compound prepared in example 1 (150 mg) in N,N-dimethylformamide (10 ml). The mixture was stirred at room temperature for 2 hour, under atmosphere of hydrogen. The reaction mixture was filtered through celite and the filtrate was concentrated. Ether was added into the residue. The solution was filtered and the filtrate was concentrated. Ether was added into the residue, crystals were filtered and dried to give the title compound (80 mg) having the following physical data.

TLC: Rf 0.21 (Chloroform: Methanol: Acetic acid=9:1:0.5), NMR (CD$_{30}$D+DMSO-d6): δ 8.10–7.70 (6H, m), 7.34 (2H, d, J=7.81 Hz), 3.48 (2H, s), 2.43 (3H, s).

Example 2(1)–2(4)

The compounds having the following physical data were obtained by the same procedure as a series of reactions of example 2, using the compound prepared in example 1(1)–1(4) instead of the compound prepared in example 1.

Example 2(1)

N-Hydroxy-N-[N'-[[4-(benzoylamino)phenyl]sulfonyl]glycyl]amide

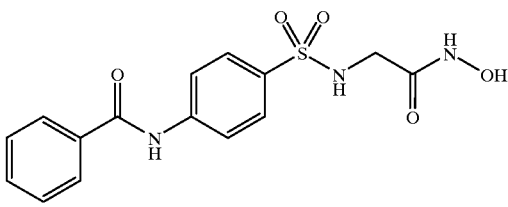

TLC: Rf 0.04 (Chloroform: Methanol: Acetic acid: Water=100:10:1:1), NMR (DMSO-d6): δ 10.58 (1H, s), 10.53 (0.5H, s), 8.86 (0.5H, s), 8.0–7.95 (4H, m), 7.9–7.75 (2H, m), 7.6–7.5 (3H, m), 3.33 (2H, s).

Example 2(2)

N-Hydroxy-N-[N'-[[4-(4-methoxybenzoylamino)phenyl]sulfonyl]glycyl]amide

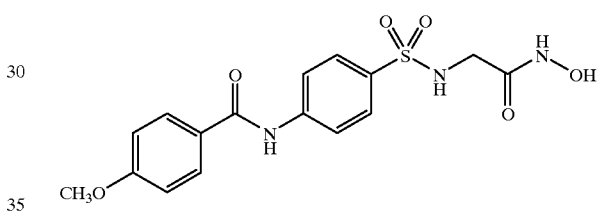

TLC: Rf 0.38 (Chloroform Methanol: Acetic acid=16:3:1), NMR (DMSO-d6): δ 10.52 (1H, s), 10.40 (1H, s), 8.86 (1H, s), 7.97 (4H, d, J=8.8 Hz), 7.90–7.70 (1H), 7.76 (2H, d, J=8.8 Hz), 7.07 (2H, d, J=8.8 Hz), 3.85 (3H s), 3.40–3.10 (2H).

Example 2(3)

N-Hydroxy-N-[N'-[[4-(4-pentylbenzoylamino)phenyl]sulfonyl]-D-phenylalanyl]amide

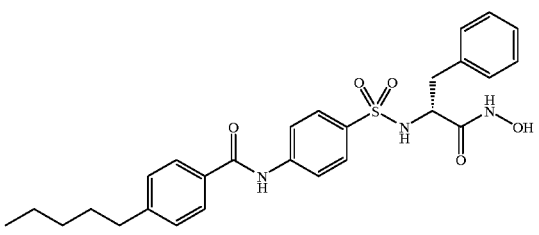

TLC: Rf 0.42 (Chloroform: Methanol=9:1), NMR (DMSO-d6): δ 10.41 (1H, s), 7.88 (2H, d, J=8.4 Hz), 7.84 (2H, d, J=8.4 Hz), 7.54 (2H, d, J=8.4 Hz), 7.35 (2H, d, J=8.4 Hz), 7.26–7.00 (5H, m), 3.77 (1H, t, J=6.6 Hz), 2.90–2.72 (1H, m), 2.72–2.56 (3H, m), 1.70–1.50 (2H, m), 1.50–1.10 (4H, m), 0.87 (3H, t, J=6.8 Hz).

Example 2(4)

N-Hydroxy-N-[N'-[[4-(p-toluoylamino)phenyl]sulfonyl]-D-tryptophyl]amide

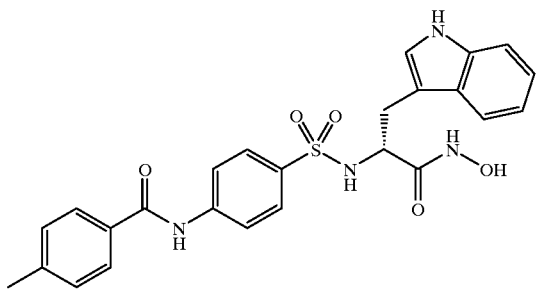

TLC: Rf 0.59 (Chloroform: Methanol=4:1), NMR (DMSO-d6): δ 10.74 (1H, s), 10.59 (1H, s),10.38 (1H, s), 8.80 (1H, s),8.02–7.80 (5H, m), 7.58 (2H, d, J=8.6 Hz), 7.38–7.23 (4H, m), 7.00–6.85 (1H, m), 3.90–3.74 (1H, m), 3.04–2.90 (1H, m), 2.75–2.61 (1H, m), 2.40 (3H, s).

Example 3

N-Hydroxy-N-[N'-[[3-(benzoylamino)phenyl]sulfonyl]glycyl]amide

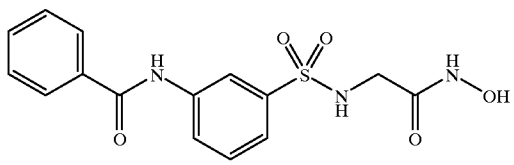

1, 1'-Carbonyldiimidazole (265 mg) was added to a solution of the compound prepared in reference example 4(5) (500 mg) in tetrahydrofuran(15 ml). The mixture was stirred at room temperature for 7 hours. Hydroxylamine hydrochloride (213 mg) was added to the reaction mixture, and the mixture was stirred at room temperature for 18 hours. 1N Hydrochloric acid was added to the reaction mixture. The mixture was extracted with ethyl acetate. The extract was washed with water and a saturated aqueous solution of sodium chloride, dried and concentrated. The residue was washed with ether and dried to give the title compound (391 mg) having the following physical data.

TLC: Rf 0.46 (Chloroform: Methanol: Acetic acid= 16:3:1), NMR (DMSO-d6): δ 10.55 (2H, s), 8.88 (1H, s), 8.33 (1H, s), 8.09–7.90 (4H, m), 7.64–7.48 (5H, m), 3.40–3.30 (2H).

Example 3(1)–3(2)

The compounds having the following physical data were obtained by the same procedure as a series of reactions of example 3, using the compound prepared in reference example 4(6) and 4(7) instead of the compound prepared in reference example 4(5).

Example 3(1)

N-Hydroxy-N-[N'-[[2-(benzoylamino)phenyl]sulfonyl]glycyl]amide

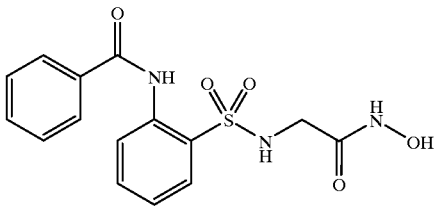

TLC: Rf 0.40 (Ethyl acetate), NMR (DMSO-d6): d 10.60 (1H, s), 10.32 (1H, s), 9.05–8.80 (1H, br.s), 8.57 (1H, t, J=6.0 Hz), 8.50–8.41 (1H, m), 8.03–7.93 (2H, m), 7.90–7.82 (1H, m), 7.74–7.52 (4H, m), 7.40–7.28 (1H, m), 3.41 (2H, d, J=6.0Hz).

Example 3(2)

N-Hydroxy-N-[N'-[[2-(2-thienylcarbonylamino)phenyl]sulfonyl]-D, L-alanyl]amide

TLC: Rf 0.48 (Chloroform: Methanol=4:1), NMR (DMSO-d6): δ 10.57 (1H, br.s), 8.84 (1H, d, J=2.2 Hz), 8.11 (1H, d, J=3.6Hz), 7.97–7.88 (5H, m), 7.76 (2H, d, J=8.8 Hz), 7.24 (1H, t, J=3.6 Hz), 3.68–3.61 (1H, m), 1.02 (3H, d, J=7.2 Hz).

Formulation Example 1

The following components were admixed in conventional method and punched out to obtain 100 tablets each containing 50 mg of active ingredient.

N-Hydroxy-N-[N'-[[4-(p-toluoylamino)phenyl]sulfonyl]glycyl]amide 5 g
Carboxymethyl Cellulose calcium (disintegrating agent) 0.2 g
Magnesium stearate (lubricating agent) 0.1 g
Microcrystalline cellulose 4.7 g

Formulation Example 2

The following components were admixed in conventional method. The solution was sterilized in conventional manner, placed 2 ml portions into 5 ml ampoules and freeze-dried to obtain 100 ampoules each containing 20 mg of the active ingredient.

N-hydroxy-N-[N'-[[4-(p-toluoylamino)phenyl]sulfonyl]glycyl]amide 2.00 g
mannitol 20 g
distilled water 500 ml

What is claimed is:

1. A hydroxamic acid derivative of formula (I):

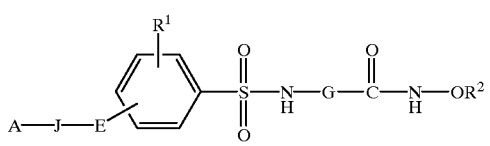

wherein $R^1$ is hydrogen, or C1–4 alkyl;

$R^2$ is (1) hydrogen, (2) C1–8 alkyl, (3) phenyl, or (4) C1–4 alkyl substituted by phenyl;

E is (1) —CONR$^3$—, in which $R^3$ is hydrogen, C1–4 alkyl, phenyl, or C1–4 alkyl substituted by phenyl;

(2) —NR$^3$CO—, in which $R^3$ is as hereinbefore defined;

(3) —CO—O—, (4) —O—CO—, (5) —NR$^3$—CO—NR$^3$—, in which $R^3$ is as hereinbefore defined;

(6) —CO—CH$_2$—, (7) —CO—, (8) —O—C O—NR$^3$—, in which is as hereinbefore defined;

(9) —NR$^3$—CO—O—O—, in which $R^3$ is as hereinbefore defined;

(10) —O—CO—O—,

(11) —CS—NR$^3$—, in which $R^3$ is as hereinbefore defined;

(12) —NR$^3$—CS—, in which $R^3$ is as hereinbefore defined;

(13) —NR$^3$—CS—NR$^3$—, in which $R^3$ is as hereinbefore defined;

(14) —O—CS—NR$^3$—, in which $R^3$ is as hereinbefore defined;

(15) —NR$^3$—CS—O—, in which $R^3$ is as hereinbefore defined;

(16) —CS—O—,

(17) —O—CS—, or

(18) —O—CS—O—,

A is (1) hydrogen, (2) C1–8 alkyl, (3) C3–7 cycloalkyl, or (4) Ar, in which Ar is carbocyclic aryl or heterocyclic aryl, and is unsubstituted or substituted by 1–3 of C1–15 alkyl, C1–15 alkoxy, halogen, nitro, cyano, guanidino, amidino, hydroxy, benzyloxy, —NR$^9$R$^{10}$, in which $R^9$ and $R^{10}$ each, independently, is hydrogen or C1–4 alkyl; —COOR$^{11}$, in which $R^{11}$ is hydrogen or C1–4 alkyl; trifluoromethyl, phenyl or heterocyclic ring;

J is (1) a bond, (2) C2–4 alkylene, (3) C2–4 alkenylene, or (4),

in which $R^4$ and $R^5$ each, independently, is (i) hydrogen, (ii) C1–4 alkyl, or (iii) C1–4 alkoxy, or $R^4$ and $R^5$, taken together with the carbon to which they are attached, form a C3–7 cycloalkyl group, G is (1) —(CH$_2$)$_m$—, in which m is 2, 3 or 4, or (2)

in which $R^6$ and $R^7$ each, independently, is (i) hydrogen, (ii) C1–8 alkyl, (iii) —COOR$^8$, in which $R^8$ is hydrogen, C1–8 alkyl, phenyl, or C1–4 alkyl substituted by phenyl; (iv) Ar, in which Ar is as hereinbefore defined; (v) heterocyclic ring, (vi) C1–8 alkyl substituted by: —COOR$^8$, in which $R^8$ is as hereinbefore defined; C1–4 alkoxy; hydroxy; benzyloxy; —NR$^{12}$R$^{13}$, in which $R^{12}$ and $R^{13}$ each, independently, is hydrogen or C1–4 alkyl; —NR$^{14}$COOR$^{15}$, in which $R^{14}$ is hydrogen or C1–4 alkyl, and $R^{15}$ is hydrogen, C1–8 alkyl, phenyl, or C1–4 alkyl substituted by phenyl; Ar; or heterocyclic ring; with the proviso that one of the carbon atoms in C1–8 alkyl may be replaced by a sulfur atom; or $R^6$ and $R^7$, taken together with the carbon to which they are attached, form a C3–7 cycloalkyl group; with the proviso that, the compounds in which E is —O—CO—NR$^3$—, —O—CO—O—, —O—CS—NR$^3$— or —O—CS—O—, J is a bond and A is hydrogen are excluded; and non-toxic salts thereof.

2. A compound according to claim 1, wherein E is —CONR$^3$—, —NR$^3$CO—, —NR$^3$—CO—NR$^3$—, —O—CO—NR$^3$—, —NR$^3$—CO—O—, —CS—N R$^3$—, —NR$^3$—CS—, —NR$^3$—CS—NR$^3$—, —O—CS—NR$^3$— or —NR$^3$—CS—O—.

3. A compound according to claim 1, wherein E is —CO—O—, —O—CO—, —CO—CH$_2$—, —CO—, —O—CO—O—, —CS—O—, —O—CS— or —O—CS—O—.

4. A compound according to claim 1, which is selected from

N-Benzyloxy-N-[N'-[[4-(p-Toluoylamino)phenyl]sulfonyl]glycyl]amide,

N-Benzyloxy-N-[N'-[[4-(benzoylamino)phenyl]sulfonyl]glycyl]amide,

N-Benzyloxy-N-[N'-[[4-(4-methoxybenzoylamino)phenyl]sulfonyl]glycyl]amide,

N-Benzyloxy-N-[N-[[4-(4-pentylbenzoylamino)phenyl]sulfonyl]-D-phenylalanyl]amide, N-Benzyloxy-N-[N'-[[4-(p-toluoylamino)phenyl]sulfonyl]-D-tryptophyl]amide, N-Hydroxy-N-[N'-[[4-(p-toluoylamino)phenyl]sulfonyl]glycyl]amide, N-Hydroxy-N-[N'-[[4-(benzoylamino)phenyl]sulfonyl]glycyl]amide, N-Hydroxy-N-[N'-[[4-(4-methoxybenzoylamino)phenyl]sulfonyl]glycyl]amide, N-Hydroxy-N-[N'-[[4-(4-pentylbenzoylamino)phenyl]sulfonyl]-D-phenylalanyl]amide, N-Hydroxy-N -[N'-[[4-(p-toluoylamino)phenyl]sulfonyl]-D-tryptophyl]amide, N-Hydroxy-N-[N'-[[3-(benzoylamino)phenyl]sulfonyl]glycyl]amide, N-Hydroxy-N-[N'-([2-(benzoylamino)phenyl]sulfonyl]glycyl]amide, and N-Hydroxy-N-[N'-[[2-(2-thienylcarbonylamino)phenyl]sulfonyl]-D,L-alanyl]amide, and non-toxic salts thereof.

5. A pharmaceutical composition for the prevention and treatment of diseases induced by overexpression or excess activation of gelatinases which are rheumatoid diseases, arthrosteitis, abnormal bone resorption, osteoporosis, periodontitis, interstitial nephritis, arteriosclerosis, pulmonary emphysema, cirrhosis, cornea injury, transfer, infiltration or growth of tumor cells, autoimmune disease (Crohn's disease, Sjogren's syndrome), disease caused by vascular emigration or infiltration of leukocytes, arterialization, which comprises, as active ingredient, an effective amount of hydroxamic acid derivatives of the formula (I) depicted in claim 1 or the pharmaceutically acceptable salt thereof, with a pharmaceutical carrier or coating.

6. A method for the prevention and treatment of diseases induced by overexpression or excess activation of gelatinases which are rheumatoid diseases, arthrosteitis, abnormal bone resorption, osteoporosis, periodontitis, interstitial nephritis, arteriosclerosis, pulmonary emphysema, cirrhosis, cornea injury, transfer, infiltration or growth of tumor cells, autoimmune disease (e.g. Crohn's disease, Sjogren's syndrome), disease caused by vascular emigration or infiltration of leukocytes, arterialization, which comprises the administration of an effective amount of hydroxamic acid of the formula (I) or non-toxic salts thereof.

* * * * *